US006906296B2

(12) United States Patent
Centanni et al.

(10) Patent No.: US 6,906,296 B2
(45) Date of Patent: Jun. 14, 2005

(54) ELECTROMAGNETICALLY RESPONSIVE HEATING APPARATUS FOR VAPORIZER

(75) Inventors: Michael A. Centanni, Parma, OH (US); Aaron L. Hill, Erie, PA (US); Francis J. Zelina, Lake City, PA (US)

(73) Assignee: STERIS Inc., Temecula, CA (US)

( * ) Notice: Subject to any disclaimer, the term of this patent is extended or adjusted under 35 U.S.C. 154(b) by 0 days.

(21) Appl. No.: 10/815,315

(22) Filed: Apr. 1, 2004

(65) Prior Publication Data

US 2004/0182855 A1 Sep. 23, 2004

Related U.S. Application Data

(63) Continuation-in-part of application No. 10/167,910, filed on Jun. 12, 2002, now Pat. No. 6,734,405.

(51) Int. Cl.[7] ................................................. H05B 6/10
(52) U.S. Cl. ..................... 219/628; 219/629; 219/635; 422/22
(58) Field of Search ........................... 219/628–631, 219/634, 635, 688, 730, 759; 422/22, 26–27

(56) References Cited

U.S. PATENT DOCUMENTS

| | | | |
|---|---|---|---|
| 4,013,742 A | 3/1977 | Lang | 261/130 |
| 4,236,056 A | 11/1980 | Allen et al. | 219/10.55 |
| 4,310,738 A | 1/1982 | Moretti et al. | 219/10.55 |
| 4,341,936 A * | 7/1982 | Virgin | 219/630 |
| 4,431,890 A | 2/1984 | Ramer | 219/10.51 |
| 4,678,881 A | 7/1987 | Griffith | 219/10.51 |
| 4,756,882 A | 7/1988 | Jacobs et al. | 422/23 |
| 5,222,185 A | 6/1993 | McCord, Jr. | 392/314 |
| 5,286,942 A | 2/1994 | McFadden et al. | 219/630 |
| 5,324,904 A | 6/1994 | Cresswell et al. | 219/635 |
| 5,378,879 A * | 1/1995 | Monovoukas | 219/634 |
| 5,523,550 A | 6/1996 | Kimura | 219/772 |
| 5,750,072 A | 5/1998 | Sangster et al. | 422/22 |
| 5,773,798 A | 6/1998 | Fukumura | 219/631 |
| 5,949,958 A | 9/1999 | Naperkowski et al. | 392/399 |
| 5,969,928 A | 10/1999 | Hashimoto et al. | 361/106 |
| 6,008,482 A | 12/1999 | Takahashi et al. | 219/687 |
| 6,023,054 A * | 2/2000 | Johnson, Jr. | 219/634 |
| 6,094,523 A | 7/2000 | Zelina et al. | 392/399 |
| 6,237,576 B1 | 5/2001 | Buccino et al. | 123/549 |
| 6,271,509 B1 * | 8/2001 | Dalton | 219/687 |
| 6,734,405 B2 | 5/2004 | Centanni et al. | 219/628 |
| 2001/0053283 A1 | 12/2001 | Levine et al. | 392/395 |
| 2003/0205571 A1 | 11/2003 | Flugstad et al. | 219/497 |

FOREIGN PATENT DOCUMENTS

| | | |
|---|---|---|
| EP | 0 884 928 | 12/1998 |
| FR | 2713871 | 6/1995 |
| JP | 11-281005 | 10/1999 |
| JP | 11346645 | 12/1999 |

OTHER PUBLICATIONS

PCT International Search Report for PCT/US03/12621.

* cited by examiner

*Primary Examiner*—Philip H. Leung
(74) *Attorney, Agent, or Firm*—Kusner & Jaffer; Michael A. Centanni

(57) ABSTRACT

A vaporizer heating apparatus is comprised of electromagnetically responsive material and electrically non-conductive material. A antimicrobial fluid to be vaporized, such as water or hydrogen peroxide solution, is supplied to the heating apparatus where it is converted to a vapor. In one embodiment of the present invention, electromagnetically responsive material particulate is embedded into the electrically non-conductive material. In another embodiment of the present invention, a microwave generator is used to produce heat.

26 Claims, 12 Drawing Sheets

ELECTROMAGNETICALLY RESPONSIVE HEATING APPARATUS FOR VAPORIZER

RELATED APPLICATIONS

This application is a continuation-in-part of U.S. application Ser. No. 10/167,910, filed Jun. 12, 2002, now U.S. Pat. No. 6,734,405, and is hereby fully incorporated herein by reference.

FIELD OF THE INVENTION

The present invention relates generally to a vapor generator. It finds particular application in conjunction with steam and hydrogen peroxide vapor systems used in connection with medical device disinfection and sterilization and in the sanitation, disinfection, and sterilization of rooms, buildings, large enclosures, and bottling, packaging, and other production lines and will be described with particular reference thereto. It should be appreciated, however, that the invention is also applicable to other chemical vaporization systems such as those employing other peroxides, peracids, and the like.

BACKGROUND OF THE INVENTION

A variety of microbial decontamination processes employ sterilizing vapors, such as steam or a mixture of water vapor with another antimicrobial (e.g., hydrogen peroxide vapor), in relatively large quantities. Steam sterilizers, for example, employ pressurized high temperature dry steam as a sterilizing vapor. Dry steam is preferred, as unvaporized water droplets can shield microbes or prions from the steam. Hydrogen peroxide vapor systems use a flow of hydrogen peroxide vapor, typically at around atmospheric pressure or below. Again, the presence of water droplets is not beneficial, as they can shield microbes and prions from the peroxide vapor.

Medical, pharmaceutical, dental, and food packaging items are often sterilized prior to use or reuse, in such systems. Vapors are also used in the decontamination of sterile enclosures and other clean rooms used by hospitals and laboratories. Processing equipment for pharmaceuticals and food, freeze driers, and meat processing equipment are also advantageously disinfected or sterilized with a vapor.

In the case of steam, for example, microbial decontamination systems often create the steam by boiling water inside a reservoir of a steam generator, such as a boiler. A large heating element is usually located over the bottom surface of the reservoir to maintain a supply of boiling water.

In the case of other water-based antimicrobial vapors, such as hydrogen peroxide vapor, a vaporizer outside the chamber generates a flow of vapor. Typically, a solution of about 35% hydrogen peroxide in water is injected into the vaporizer as fine droplets or a mist through injection nozzles. The droplets contact a heated surface which heats the droplets to form the vapor, without breaking the hydrogen peroxide down to water and oxygen. A carrier gas is circulated over the heat transfer surface to absorb the peroxide vapor.

Such vapor generation methods have disadvantages when large quantities of vapor are desired or vapor is needed at short notice. Boilers tend to be relatively large pieces of equipment, which work best when the wattage is spread out over a large heating element surface area. This keeps the watt density low and extends the life of the heating element. The large heating element surface area, however, takes up considerable space. Additionally, to avoid damage to the heating element, it is completely immersed in water. Thus, it takes some time to heat the large volume of water to steam temperature in order for steam generation to begin. It is expensive to maintain a supply of over 100° C. water ready for a demand. Any unused heated water generally has to be cooled in a heat exchanger before it is disposed of in a municipal waste water system.

Vaporized hydrogen peroxide is a particularly useful vapor sterilant for both vacuum sterilizing systems and rooms and other large enclosures. It is effective at or close to room temperature, which reduces the potential for thermal degradation of associated equipment and items to be sterilized or disinfected within the sterilizer enclosure. In addition, hydrogen peroxide readily decomposes to water and oxygen, thus simplifying disposal.

As the size of the sterilizer or enclosure increases, or the demand for hydrogen peroxide is increased, the efficiency of the vaporization system becomes more significant. The capacity of the vaporizer is limited in a number of ways. First, the vaporization process creates a pressure increase, reducing the flow of the carrier gas through the vaporizer. Second, to maintain sterilization efficiency, the pressure at which the vapor is generated is limited to that at which the hydrogen peroxide is stable in the vapor state. Third, the time taken to generate the hydrogen peroxide is dependent on the time taken to heat a surface to the vaporization temperature of hydrogen peroxide.

One solution has been to increase the size of the vaporizer, the injection rate of hydrogen peroxide into the vaporizer, and the flow rate of carrier gas. However, the carrier gas tends to cool the heating surface, disrupting the vaporization process. Heating the surface to a higher temperature breaks down the hydrogen peroxide.

Yet another solution is to use multiple vaporizers to feed a single enclosure. The vaporizers may each be controlled independently, to allow for variations in chamber characteristics. However, the use of multiple vaporizers adds to the cost of the system and requires careful monitoring to ensure that each vaporizer is performing with balanced efficiency. None of these solutions addresses the initial warm up time needed for raising the temperature of the vaporizer to the vaporization temperature.

The present invention provides new and improved vaporization systems and methods which overcome the above-referenced problems and others.

SUMMARY OF THE INVENTION

In accordance with the present invention, there is provided a vaporizer for vaporizing a fluid to form an antimicrobial vapor, comprising: (1) a source of electromagnetic radiation; and (2) a heating apparatus for producing heat to vaporize an antimicrobial fluid passing therethrough, including: (a) an electrically non-conductive material, and (b) an electromagnetically responsive material.

One advantage of the present invention is that a high output of sterilant vapor is achieved.

Another advantage of the present invention is that it enables sterilant vapor to be generated "on demand" at short notice.

Another advantage resides in reduced resistive electrical power loads.

Another advantage of the present invention is that it enables vapor concentration levels to be raised rapidly, particularly when used with smaller enclosures, thereby reducing the conditioning time.

Still another advantage of the present invention is the provision of a vaporizer constructed of materials that will not degrade antimicrobial fluids.

A still further another advantage of the present invention is the provision of a vaporizer having reduced weight.

Yet another advantage of the present invention is the provision of a vaporizer that is less costly to manufacture.

These and other advantages will become apparent from the following description of preferred embodiments taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

The invention may take form in various components and arrangements of components, and in various steps and arrangements of steps. The drawings are only for purposes of illustrating a preferred embodiment and are not to be construed as limiting the invention.

DETAILED DESCRIPTION OF A PREFERRED EMBODIMENT

Figure 1:
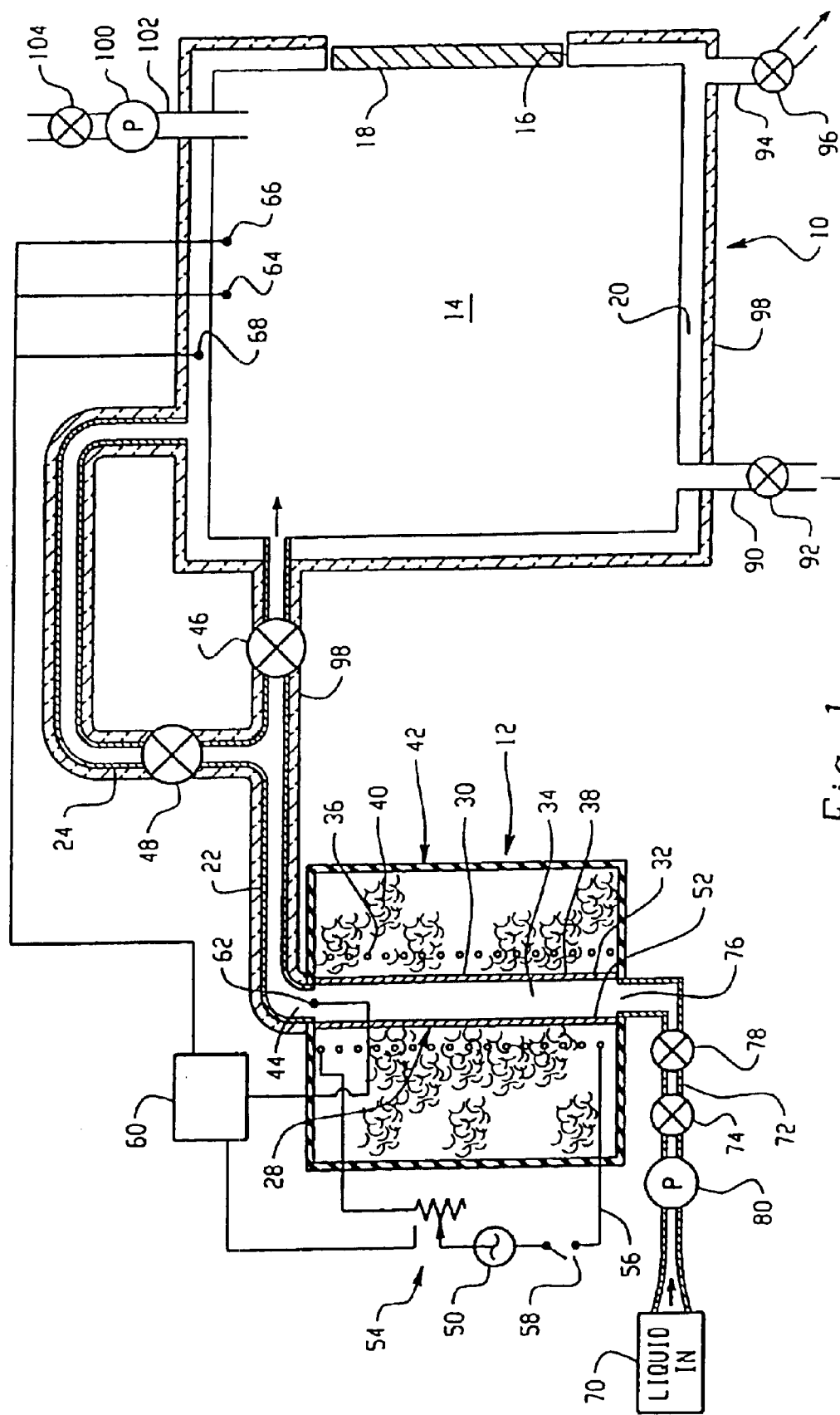
FIG. 1 is a schematic view of a first embodiment of a vaporization system in accordance with the present invention.

Referring now to the drawings wherein the showings are for the purposes of illustrating a preferred embodiment of the invention only and not for purposes of limiting same, FIG. 1 shows a system for providing an antimicrobial vapor to a sterilization chamber or for microbially decontaminating a room or other defined area with an antimicrobial vapor. While the system is described with particular reference to steam and to hydrogen peroxide in vapor form, other antimicrobial vapors are also contemplated, such as vapors comprising peracetic acid or other peroxy compounds, aldehydes, such as formaldehyde vapors, and combinations of vapors, such as hydrogen peroxide with peracetic acid, and the like.

While particular reference is made to sterilization, which refers to the destruction of all microorganisms, whether harmful or not, it is to be appreciated that the antimicrobial vapor is alternatively used to provide lesser levels of microbial decontamination, such as disinfection or sanitization. The term "microbial decontamination" and similar terms, as used herein, include the destruction of microorganisms, such as bacteria and fungi. The term is also intended to encompass the degradation or deactivation of other harmful microorganism-sized biological species, and smaller replicating species, particularly those capable of undergoing conformational changes, such as prions.

FIG. 1 illustrates a system particularly suited to the generation of steam under pressure for a steam sterilizer 10. The system includes a vapor generator, such as a flash vaporizer 12, in close proximity to a chamber 14 of the sterilizer 10. Items to be microbially decontaminated are loaded into the chamber 14 through an opening 16 closed by a door 18. Steam from the generator 12 is supplied both to the interior chamber 14 and to a heating jacket 20, which surrounds the chamber. The system is supplied via piping, such as thermally insulated tubes or passageways 22 and 24, respectively.

The generator 12 includes an induction vessel 28, which is positioned in a magnetic field and is heated by electric currents inductively generated in the induction vessel by the magnetic field. The induction vessel 28 transfers heat generated to the liquid to be vaporized, either by conduction, radiation, or convection, which causes the liquid to be converted to vapor.

In a first embodiment, shown in FIG. 1, the induction vessel 28 comprises a heating tube 30. The heating tube 30 has a hollow tube wall 32 defining an interior passage or bore 34, which is preferably cylindrical in shape. The tube 30 is formed from an electrically and thermally conductive material, such as iron, carbon steel, stainless steel, aluminum, copper, brass, bronze, electrically conductive ceramic and polymer composites, or other materials capable of being inductively heated. As further described below, the bore 34 provides a chamber for receiving a liquid, such as water, to be converted to a vapor, such as steam. The bore 34 is sized to receive a volume of water that is sufficiently small to be vaporized rapidly as it enters and contacts walls of the bore in a flash vaporization process. While the bore 34 is shown in FIG. 1 as being vertically aligned along its axis, it is to be appreciated that the bore is alternatively horizontally aligned or have portions of the bore which are arranged in different orientations, as is discussed in further detail below. An induction coil 36 is wrapped around an outer surface 38 of the tube 30 in a helix, along all or a portion of the tube length. The coil 36 is preferably spaced from the tube by a layer 40 of thermal insulation material. An electrically insulative housing 42 surrounds the coil and insulation material.

An upper end or outlet 44 of the heating tube 30 is fluidly connected with the tubes 22, 24. Valves 46, 48 in the tubes 22, 24 variably adjust the amount of steam passing to the chamber 14 and heating jacket 20, respectively. The tubes, 22, 24, or a fitting (not shown) connecting the piping with the heating tube 30, may be formed of materials, such as copper, brass, or polymeric pipes.

An AC source 50 supplies an alternating current to the coil 36. In response to the applied current, the coil 36 produces an alternating magnetic field, which passes through the heating tube 30, causing eddy currents which heat the tube. The heat passes through to an inner surface 52 of the tube 30 in contact with the water droplets moving through the bore 34. The electrical current, and hence the rate of heating of the heating tube 30, is adjustable, for example, by the provision of an adjustment means 54, such as a pulse width modulator, a variable resistor, or the like in an electrical circuit 56 connecting the AC source 50 and the induction coil 36. Alternatively, or additionally, the adjustment means includes a simple on/off switch 58 in the circuit 56.

The current adjustment means 54, 58 are preferably under the control of a control system 60, which also controls other aspects of the sterilization system. For example, the control system 60 receives steam temperature measurements from a temperature monitor 62, such as a thermocouple, positioned adjacent the outlet end of the heating tube, or elsewhere in the system such as in the passages 22, 24. The controller 60 controls the current adjustment means 54, 58 in response to the measured temperature to maintain a preselected steam temperature. The controller 60 is preferably also connected with one or more of temperature monitors 64 and pressure monitors 66, 68 positioned within the chamber 14, the heating jacket 20, or elsewhere in the system. The controller regulates the generator 12 to maintain desired sterilization temperature and pressure, as is described in greater detail below.

Fresh water or other liquid to be vaporized from a source 70 such as mains water or purified water from a tank, is supplied to the generator via a liquid inlet tube or line 72, regulated by an adjustable inlet valve 74, such as a solenoid valve, which is preferably under the control of the controller 60. The inlet tube 72 is connected to a second end or inlet end 76 of the heating tube 30. As with the outlet tubes 22, 24, the inlet tube 72, or a fitting (not shown) connecting the inlet tube 72 with the heating tube 30, is preferably formed from copper, brass, or polymeric pipe. A check valve 78 in inlet line 72 is preferably provided to prevent the backflow of water out of the steam generator 12.

The inductively generated heat flash vaporizes the water located in the bore 34 to produce steam. The water is preferably introduced to the bore as a continuous stream of liquid water under pressure. The water is changed to steam as it traverses a two-phase region from a saturated liquid to a saturated gas. As steam is produced, the pressure inside the bore 34 increases. The steam is forced under pressure out of the bore and through the fluid pathway 24 connecting the generator 12 to the chamber 14. The process continues in this manner, producing more steam from the series of water injections.

In an alternative embodiment, the water, or other liquid to be vaporized, is introduced as a continuous stream.

If mains water is used, the water is preferably passed through a filter system (not shown) to remove particulate material, dissolved minerals, and/or organic matter. Purity can be expressed as the resistance between two electrodes spaced one centimeter apart in a sample of water to be tested, one meg-ohm being a resistance of $1 \times 10^6$ ohm. Preferably, the filtered or otherwise purified water has a purity of 1 meg-ohm, or higher, which may be achieved with a reverse osmosis (RO) filter followed by an ion-exchange bed. Optionally, a pump 80 pressurizes the water in the inlet line 72.

Spent steam or liquid water exits the sterilizer chamber 14 through a line 90. A steam trap 92 in the line 90 opens when condensate is present to release the condensate. Spent steam or liquid water from the jacket 20 leaves by an interconnected drain line or by a separate second drain line 94 and trap 96. Thermal insulation 98, optionally supplemented by heating tape or other heating means (not shown) where appropriate, preferably surrounds the pathways 22, 24, the heating jacket 20, and may also cover the door 18.

Optionally, a suction means 100, such as a vacuum pump or water ejector, is used to withdraw air or steam from the chamber 14, via a vacuum line 102, prior to a sterilization cycle, during the cycle, or to remove spent vapor after the sterilization cycle.

A typical sterilization process proceeds as follows. Items to be microbially decontaminated, such as medical, dental, or pharmaceutical instruments, or the like, are loaded into the chamber 14 and the door 18 closed. Steam is introduced to the chamber 14 to displace air, which passes downward and out of the chamber via the drain line 90. The controller 60 optionally controls the vacuum pump or water ejector 100 to withdraw air from the chamber 14. The controller 60 then closes valve 104 in the vacuum line 102. Optionally, several pulses of steam are applied to chamber 14, each one followed by or preceded by a vacuum pulse. For example, steam is introduced until a preselected pressure is achieved. The pump or water ejector 100 is then operated until a preselected vacuum is achieved. The pressurizing and evacuating steps are preferably repeated several times (usually about four times), ending with a steam pressurizing step.

The controller also controls the heating of the interior of the chamber by controlling operation of the generator and valve 48. Specifically, the controller receives temperature measurements from the temperature monitors 64, 68 and controls the water inlet valve 74 and/or variable resistor 54 to generate steam, which passes along the line 24 to the jacket. Once the chamber 14 is at a suitable temperature, preferably above the condensation temperature of the steam, the controller 60 opens the valve 46, allowing steam to enter the chamber. The controller 60 controls operation of the resistor 54 and various valves 46, 48, 74, 96, 104, in response to temperature and pressure measurements received from the monitors 62, 64, 66, 68, to maintain preselected sterilization conditions (e.g., temperature and pressure) for a period of time considered sufficient to effect the desired level of antimicrobial decontamination. Once the period of time has elapsed, valve 46 is closed and the steam is withdrawn from the chamber 14 by the vacuum pump 100. Fresh or filtered air is then allowed to enter the chamber 14.

Figure 2:
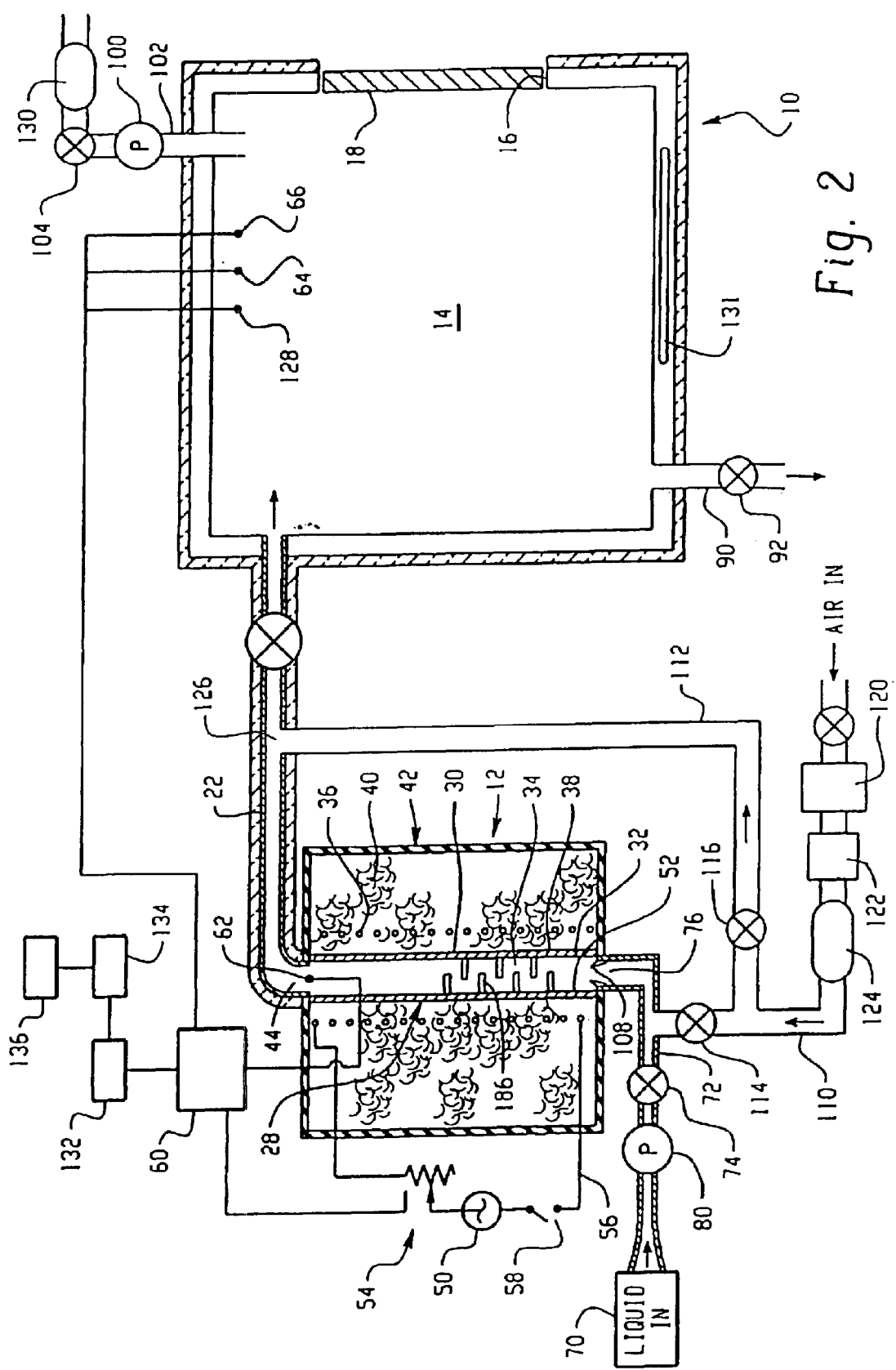
FIG. 2 is a schematic view of a second embodiment of a vaporization system according to the present invention.

In an alternative embodiment, shown in FIG. 2, the sterilization system 10 is shown adapted for microbial decontamination with hydrogen peroxide or other multi-component vapor. In this embodiment, the generator 12 is analogous to that of FIG. 1 but is used for the production of a multi-component vapor, such as a hydrogen peroxide and water vapor mixture. A liquid to be vaporized, such as an aqueous mixture of hydrogen peroxide in water, is pumped from a reservoir or tank 70 to the generator via the inlet line 72. More specifically, a means for introducing liquid hydrogen peroxide, such as an injection pump 80, pressurized container, gravity feed system, or the like, deposits hydrogen peroxide, preferably in the form of a liquid flow or spray, from the reservoir 70 into the generator 12 via an injection nozzle 108.

The liquid hydrogen peroxide includes a mixture of hydrogen peroxide in a diluent, such as water, preferably an aqueous mixture comprising about 30–40% by weight hydrogen peroxide in water.

The hydrogen peroxide vapor generated when the liquid contacts the heated wall 32 of the heating tube 30 is preferably mixed with a carrier gas. In one embodiment, a carrier gas, such as air, nitrogen, carbon dioxide, helium, argon, or a combination of carrier gases, is fed into the flash vaporizer 12 concurrently with the hydrogen peroxide liquid to assist in propelling the peroxide vapor through the vaporizer. The air enters the heating tube 30 via a carrier gas line 110, which may be connected with the liquid inlet line 72, as shown in FIG. 2, or pass directly into the bore 34. Alternatively, or additionally, a carrier gas line 112 is connected with the outlet line 22, such that the carrier gas mixes with the already formed vapor. Mixing all or most of the carrier gas with the vapor after vapor formation increases the throughput of the vaporizer. Valves 114, 116 in the carrier gas lines 110, 112 are used to regulate the flow rate of carrier gas through the lines 110, 112, respectively.

The carrier gas may be air at atmospheric pressure or supplied from a tank or other reservoir (not shown). Preferably, the incoming carrier gas is passed through a filter 120, such as an HEPA filter, to remove airborne particulates, through a dryer 122 to remove excess moisture, and is heated by a heater 124 to raise the temperature of the carrier gas.

The preferred pressure of the carrier gas supplied to lines 110, 112 varies with the production rate of hydrogen peroxide and the length and restrictiveness of passages in the flash vaporizer 12, and typically varies from 1.0–2.0 atmospheres absolute ($1.013 \times 10^5$–$2.026 \times 10^5$ Pascals absolute), i.e., about 0–1 atm. gauge (0–$1.013 \times 10^5$ Pascals gauge), more preferably, about 6–$14 \times 10^3$ Pa.

The flash vaporization and sweeping carrier gas ensure that the hydrogen peroxide/water mixture does not condense and form a puddle in the vaporizer. Another advantage of using such a carrier gas to carry the liquid and vapor through the generator 12 arises because the liquid hydrogen peroxide is likely to continuously impinge on the same point in the vaporizer 12. The more dispersed the liquid hydrogen peroxide is within the vaporizer, the more readily the peroxide will be vaporized. In addition, with a well-dispersed hydrogen peroxide injection, it is less likely that specific regions of the vaporizer will experience undue cooling thereby hindering the vaporization process.

The carrier gas tends to cool the vaporizer, reducing the rate at which the aqueous hydrogen peroxide solution is vaporized. Consequently, it is desirable to maintain the carrier gas at or slightly above a minimum flow rate needed to carry the vaporized hydrogen peroxide through the vapor generator 12 without significant degradation of the peroxide vapor, but at a flow rate which is low enough such that appreciable cooling of the vaporizer by the carrier gas does not occur. Accordingly, the flow rate of carrier gas through the vapor generator 12 is preferably lower than the flow rate of carrier gas which does not pass through the vapor generator 12. The majority of the carrier gas thus travels through the passage 112 and is injected into the second carrier gas stream at a mixing zone 126 downstream of the vaporizer 12, where both the carrier gas stream and the vapor are combined prior to entering the chamber 14.

The mixture of carrier gas and vapor hydrogen peroxide passes through line 22 and into the chamber 14. A sensor 128, such as a hydrogen peroxide sensor, optionally detects the concentration of hydrogen peroxide and/or water vapor in the chamber 14. The controller receives the detected concentration measurements or signals indicative thereof and temperatures and pressures from monitors 64, 66 and regulates the supply of fresh hydrogen peroxide vapor to the chamber or other operating conditions accordingly. Alternatively, the controller is preprogrammed with expected concentrations of hydrogen peroxide or other data which allows the controller to maintain selected chamber conditions by controlling and/or measuring various parameters of the system, such as chamber temperature and pressure, hydrogen peroxide and carrier gas flow rates, and the like.

Spent vapor exits the chamber 14 via an outlet line 102 and is preferably passed through a destroyer 130, such as a catalytic converter, to convert any remaining hydrogen peroxide to oxygen and water, before releasing it to the atmosphere.

Alternatively, the outlet line 102 is coupled with the carrier gas inlet line(s) 110, 112 as a recirculating flow through system, whereby the spent vapor, preferably after passing through the catalytic converter, is returned to the inlet line 110, intermediate the filter 120 and dryer 122, or prior to the filter, such that the spent vapor is dried and heated before mixing once more with the hydrogen peroxide liquid or vapor.

In this embodiment, the sterilizing vapor, hydrogen peroxide and water in the preferred embodiment, is effective at room temperature or above room temperature and at atmospheric, subatmospheric, or above atmospheric pressures. The steam heating jacket 20 and line 24 are preferably eliminated, and, if it is desired to heat the chamber 14, a heater 131, such as a resistance heater, surrounds all or part of the chamber. The heater 131 is preferably under the control of the controller 60.

It is generally desirable to maintain the hydrogen peroxide below its saturation point to avoid condensation on the items to be sterilized. Thus, the controller 60 preferably controls the chamber conditions, such as temperature, pressure, vapor introduction rate, and so forth to maintain the hydrogen peroxide concentration close to but slightly below, its saturation level. For example, the control system 60 includes a comparator 132 (see FIG. 2) for comparing the monitored condition signals from the monitors 128, 64, 66 with preselected ideal hydrogen peroxide vapor concentration and other conditions as indicated by reference signals. Preferably, the comparator determines a deviation of each monitored condition signal from the corresponding reference signal or a reference value. Preferably, a plurality of the conditions are sensed and multiple comparators are provided. A processor 134 addresses an algorithm implementing program or pre-programmed look up table 136 with each deviation signal (or combination of deviations of different conditions) to retrieve a corresponding adjustment for the flash vaporizer 12. Other circuits for converting larger deviations to larger adjustments and smaller deviations to smaller adjustments are also contemplated. Alternately, the error calculation can be made at very short intervals with constant magnitude increases or decreases when the monitored condition is below or above the reference points.

The adjustment values are used by the controller 60 to adjust the hydrogen peroxide metering pump 80 and the carrier gas regulators 114, 116 to bring the monitored conditions to the reference values. For example, vapor injection rates are increased when a lower than desirable vapor concentration, higher temperatures, higher pressure, or the like is detected. Vapor production rates are reduced in response to higher sensed vapor concentration, lower sensed temperatures, lower pressure, and the like.

The vapor hydrogen peroxide system can be operated as an ambient or above atmospheric pressure system, in which the carrier gas and hydrogen peroxide vapor within the chamber is continually or intermittently replenished. Or, the system may be operated as a deep vacuum system, in which the chamber 14 is evacuated to a pressure of, for example about 10 torr or below, prior to introduction of hydrogen peroxide. As with the steam vapor system, one or more pulses of vapor may be introduced to the chamber 14, with vacuum pulses between them. In other respects, the system of FIG. 2 is analogous to the system of FIG. 1 and is operated in a similar manner. For sterilizing larger enclosures 14, such as rooms, additional vaporizers 12 may be employed, each one separately under the control of the controller 60.

It will be appreciated that while the multi-component vapor has been described with particular reference to hydrogen peroxide, other single component and multi-component vapors are also contemplated. Other suitable sterilizing vapors include peracids, such as peracetic acid with water, a mixture of hydrogen peroxide with peracetic acid, and the like.

Figure 3:
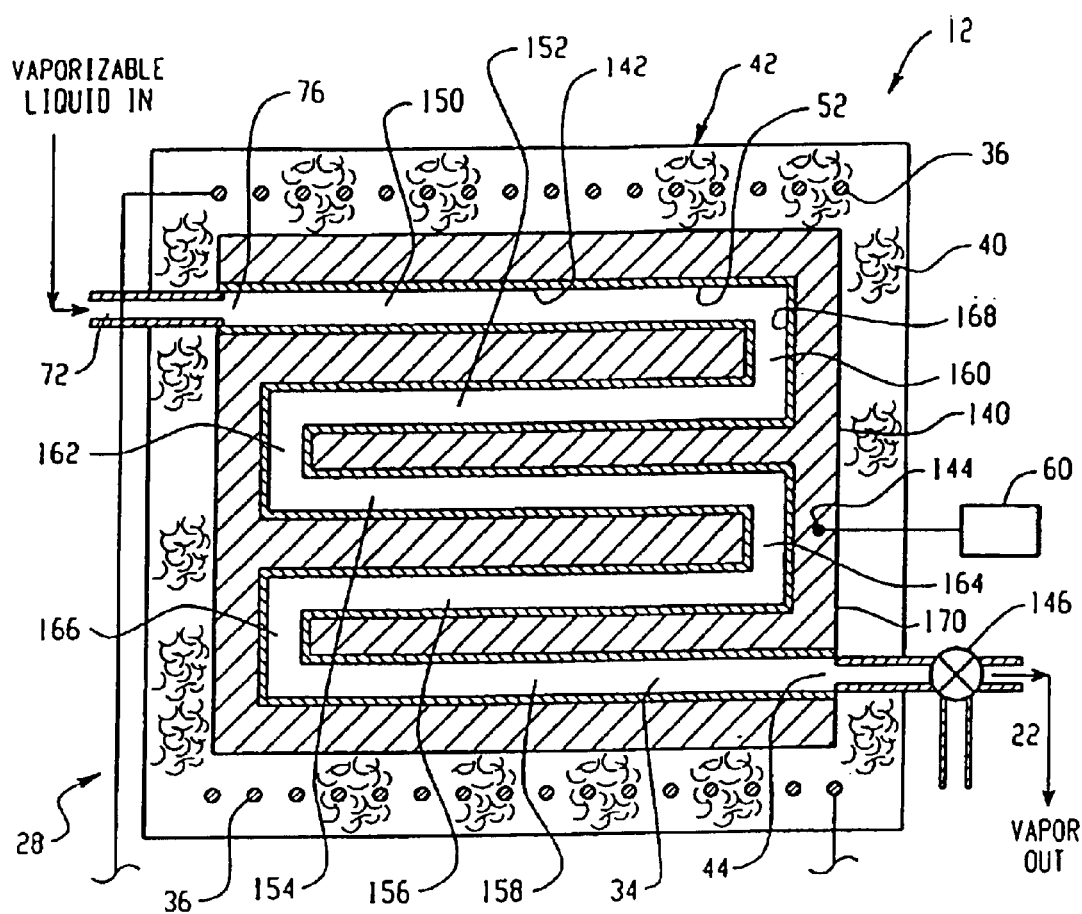
FIG. 3 is a side sectional view of a second embodiment of a vaporizer.

With reference now to FIG. 3, an alternative embodiment of a vapor generator 12 is shown. Similar components are identified by the same numerals and new components are given new numbers. In this embodiment, in place of a heating tube, the induction vessel 28 includes a bore 34 which is formed by drilling or otherwise forming a passage in a block 140 of an electrically conductive material, such as graphite, aluminum, copper, brass, bronze, steel, or the like. A coil 36 inductively heats the block 140 when an AC current is passed through the coil. Alternatively, the bore 34 is defined within tubing 142 mounted within the block 140 and in thermal contact therewith. The tubing 142 may be formed from a thermally-conductive material such as copper, brass, a polymer or a filled polymer. Alternatively, in place of tubing, the walls of the bore 34 defined by the block 140 may be coated with a layer (not shown) of a thermally conductive, protective material such as stainless steel, TEFLON™ glass, or the like, which is resistant to the liquid and vapor passing through the bore but need not be inductively heated by the coil 36. In these embodiments, heat passes from the block to the liquid by conduction through the tubing 142 or thermally conductive layer.

The induction coil 36 encircles the block 140 or a portion thereof and induces the block to heat up in a similar manner to the heating tube 30 of FIG. 1. Heat flows from the block 140 and through the tubing 142, where present. As with the embodiments of FIGS. 1 and 2, the liquid to be vaporized, e.g., aqueous hydrogen peroxide or water, either alone or with a carrier gas, passes through the generator bore 34 and is vaporized when it comes into contact with the heated walls 54 of the bore. As with the prior embodiments, thermal insulation material 40 is packed between the coil 36 and the block 140 and between the coil and the housing 42. In the case of hydrogen peroxide, the block 140 is maintained by operation of the induction coil 36 at a temperature below that at which significant dissociation of the hydrogen peroxide occurs. Optionally, an overtemperature device 144 is mounted on or in the block 140 and shuts down the power to the coil 36 in the event the coil is energized without sufficient vaporizable liquid in the block 140. In addition, a pressure release valve 146 is provided between the block 140 and the sterilization chamber 14, which releases excess pressure to protect the block and the chamber 14 from overpressure conditions.

In the embodiment of FIG. 3, the bore 34 comprises a series of elongate bore portions 150, 152, 154, 156, and 158 (four are shown in FIG. 3, although fewer or greater than four bore portions are also contemplated), which pass generally longitudinally back and forth through the block 140. The bore portions are connected by connecting or end portions 160, 162, 164, which may be positioned outside the block 140 for convenience of manufacture. End walls 168 of the end portions 160, 162, 164 are positioned generally at right angles to the direction of flow of the liquid in the bore portions. The greater inertia of flowing liquids and droplets thrown against the end walls 168, with each turn, thereby increases the rate of vaporization and reduces the chance that unvaporized droplets will be discharged from the vaporizer.

Figure 4:
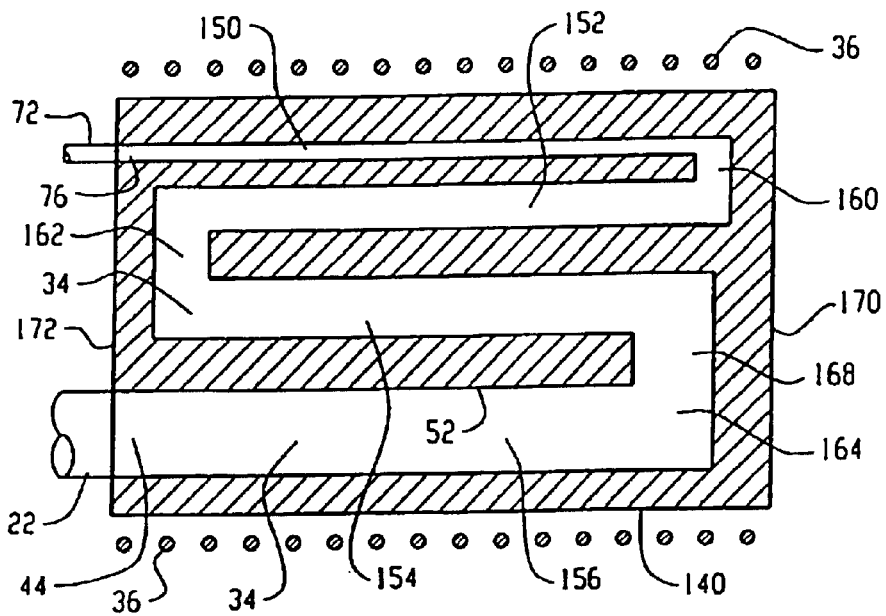
FIG. 4 is a perspective view of a third vaporizer embodiment.
Figure 5:
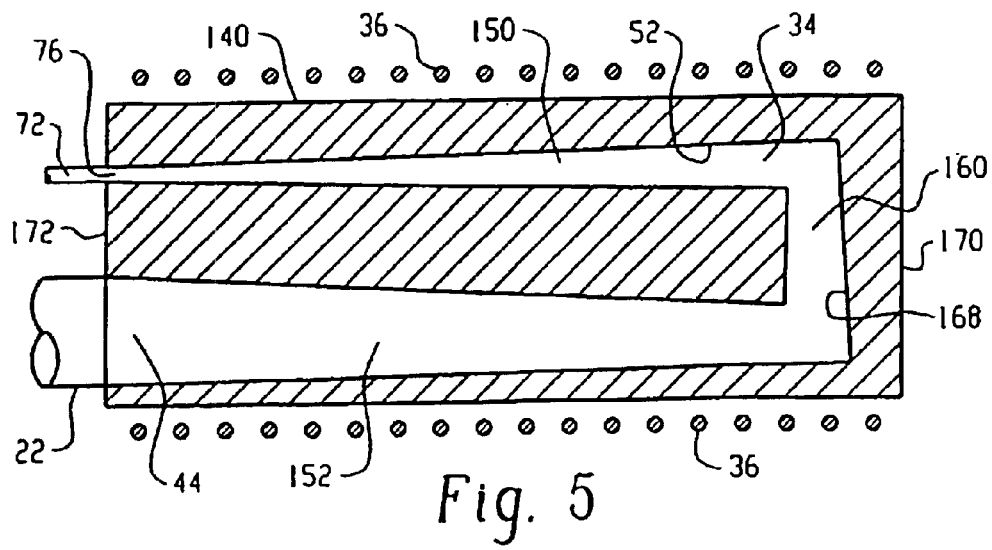
FIG. 5 is a side sectional view of a fourth embodiment of a vaporizer.

Optionally, as shown in FIGS. 4 and 5, the bore 34 increases in diameter along its length, either stepwise, with each successive bore portion 152, 154, 156 (FIG. 4), or progressively, along its length (FIG. 5), thus creating an increasing area of contact and internal volume per unit length. The liquid hydrogen peroxide contacts the wall surfaces 52 of the bore 34 and is vaporized. The increasing volume of the vapor/liquid mixture passing through the bore 34 is accommodated by the increasing diameter of the bore portions 150, 152, 154, 156, etc.

In each of the embodiments, the bore 34 may make several turns within the block 140. For example, starting at the bore inlet 76, the bore 34 makes a U-turn adjacent one end 170 of the block, returns to an inlet end 172 of the block, and optionally makes one, two, or more such turns before reaching the outlet 44. In one embodiment the turns are formed by sharp, "L-shaped" rather than rounded turns. For example, as shown in FIG. 3, each turn includes two approximately 90 degree corners adjoining the end wall 168, which turn the bore through approximately 180 degree. Having generally sharp, rather than rounded corners encourages the flowing liquid/vapor mixture to hit the walls, thereby improving the rate of vaporization.

Figure 6:
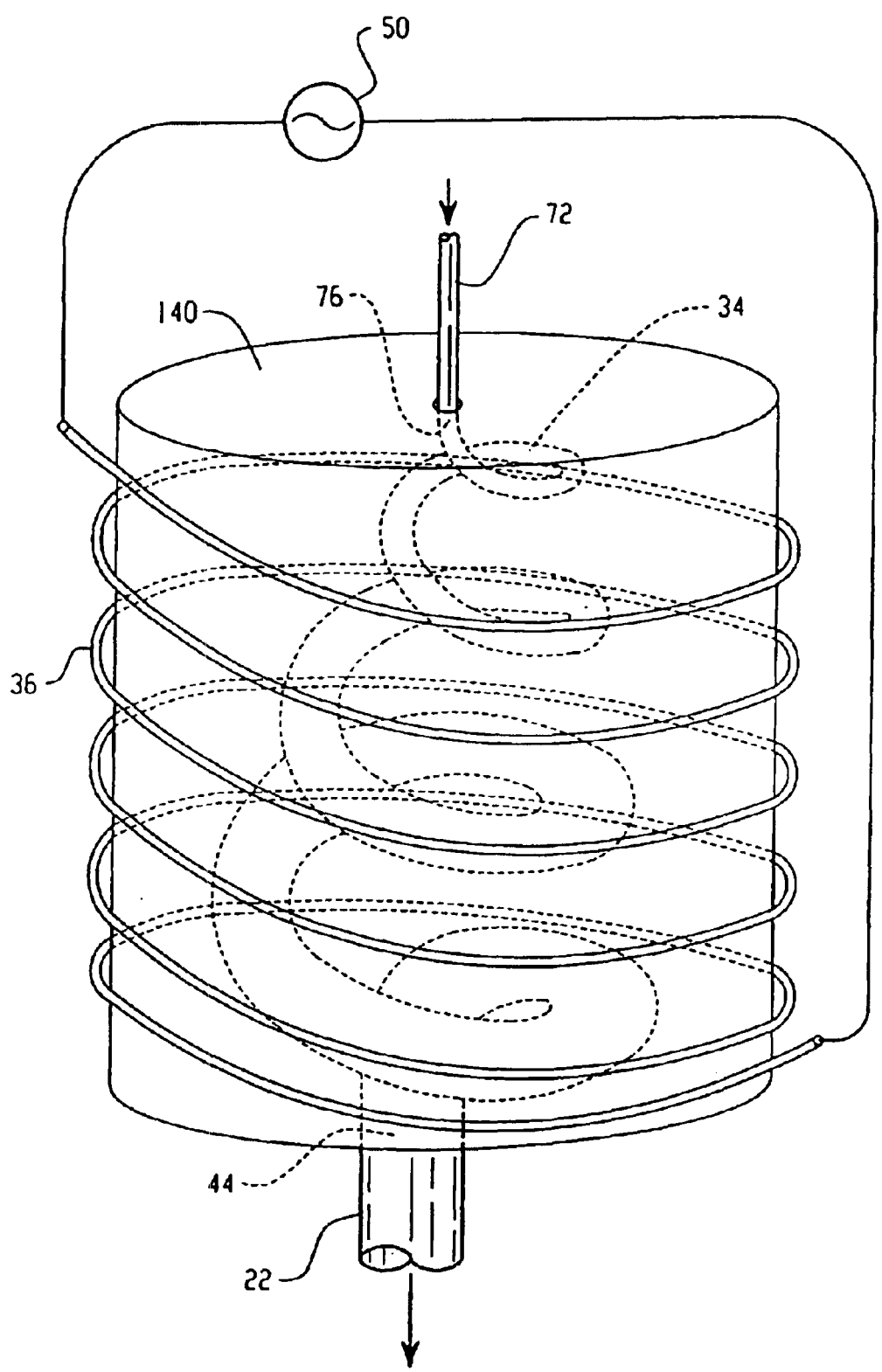
FIG. 6 is a side sectional view of a fifth embodiment of a vaporizer.

Other arrangements are contemplated, such as a spiral bore 34, as shown in FIG. 6. At each turn, inertia tends to propel fine, suspended droplets into the walls resulting in the vaporization of the droplets. In this manner, any fine droplets of mist or fog are turned to vapor. Preferably, at least two substantially 180 degree turns are provided in the flowpath to ensure this increased contact.

Figure 7:
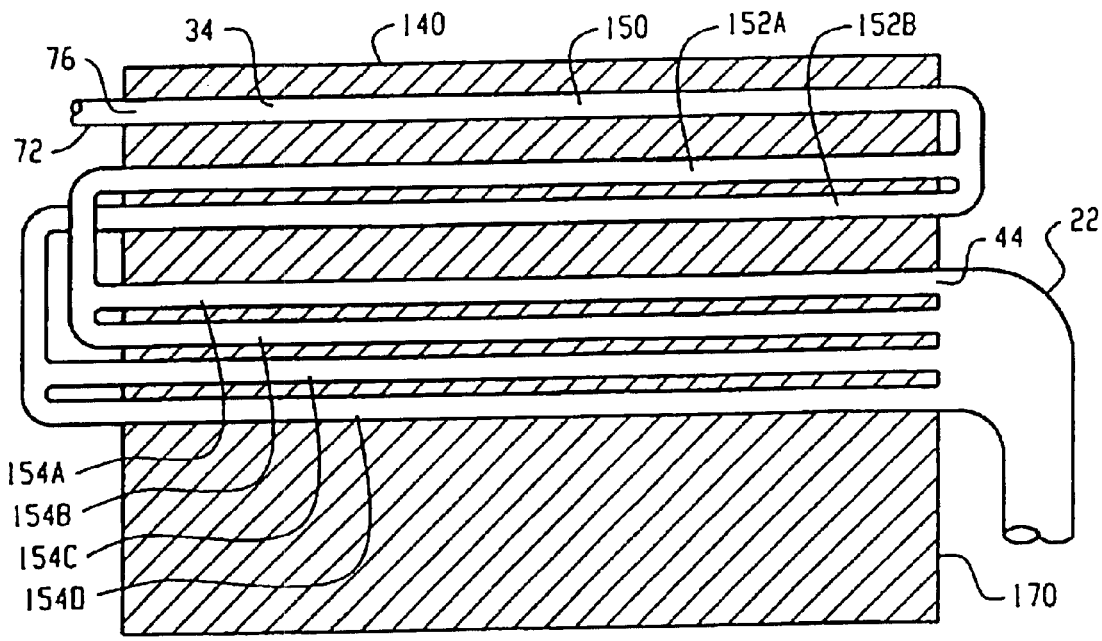
FIG. 7 is a side sectional view of a sixth embodiment of a vaporizer.

Other arrangements for progressively increasing the bore diameter are also contemplated. In the embodiment of FIG. 7, the number of bore portions increases with each pass through the block. For example, a single longitudinal bore portion 150 defines the first pass, and two or more bore portions 152A, 152B define the second pass. Each of the second bore portions 152A, 152B is preferably connected with two more bore portions 154A, 154B or 154C, 154D for a third pass, and so forth. In this way, as for the earlier embodiments, the cross sectional area of the fluid pathway 34 created by the bore portions increases as the hydrogen peroxide travels from the inlet 76 to the outlet 44 (in this case, a plurality of outlets).

Figure 8:
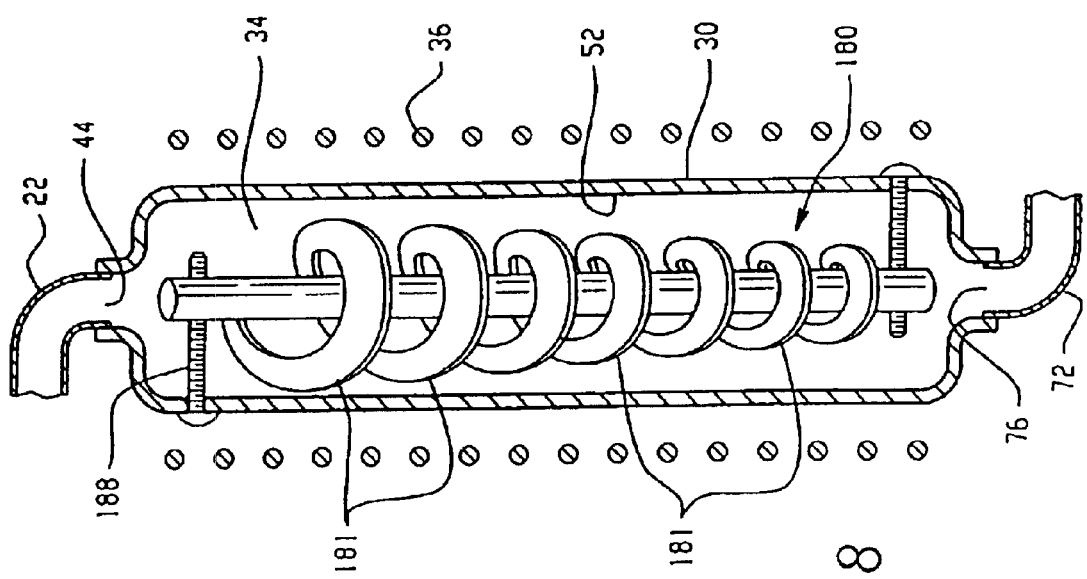
FIG. 8 is a side sectional view of a seventh embodiment of a vaporizer.
Figure 10:
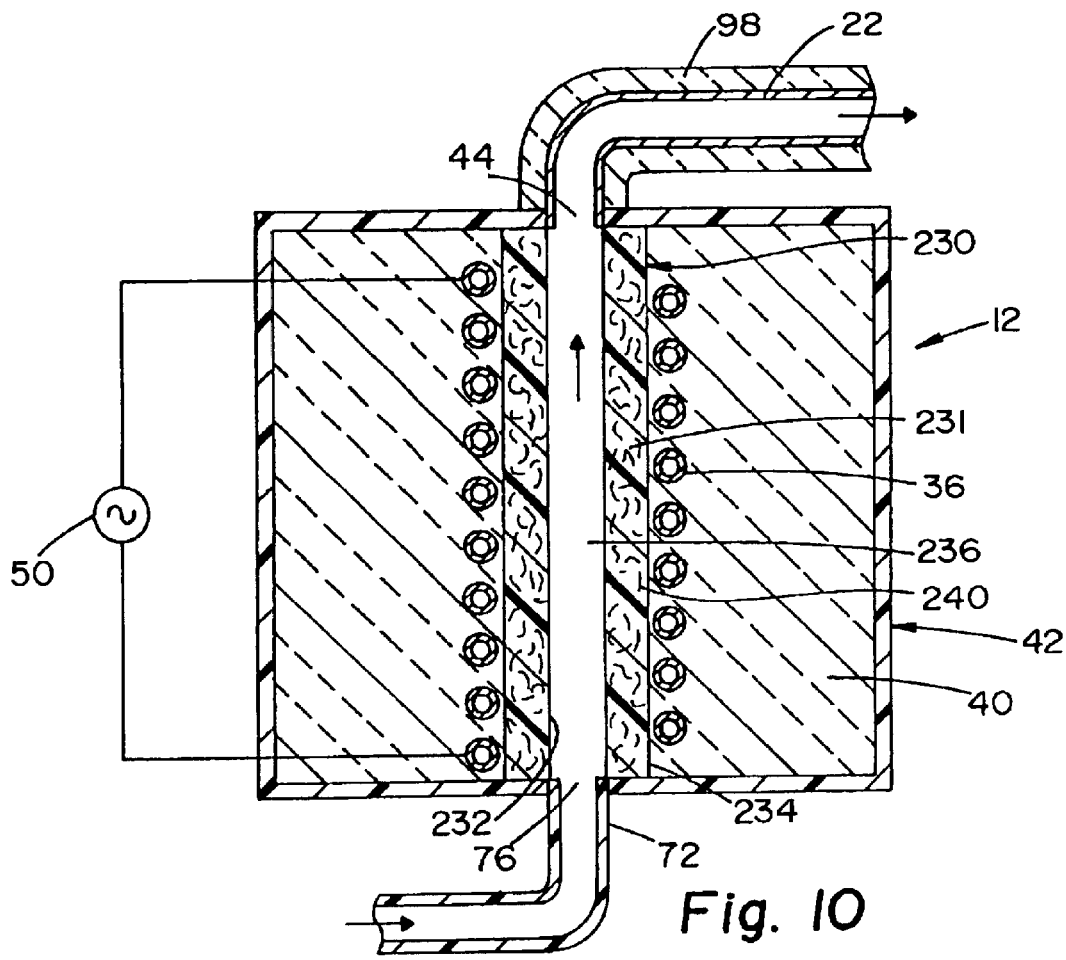
FIG. 10 is a sectional view of a vaporizer for use in a microbial decontamination process, illustrating another embodiment of the present invention.
Figure 11:
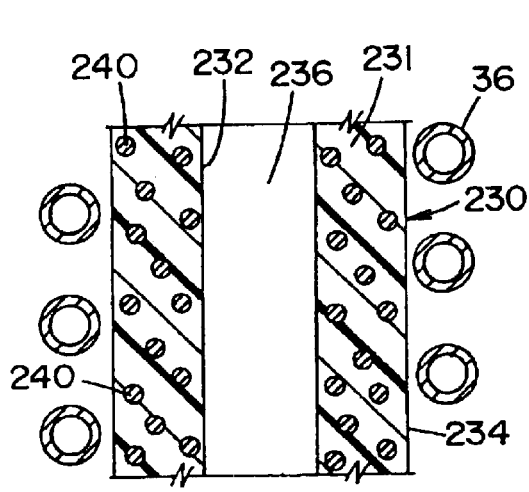
FIG. 11 is an enlarged sectional view of a portion of a vaporizer heating tube comprised of granular metal particles embedded within an electrically non-conductive material.
Figure 12:
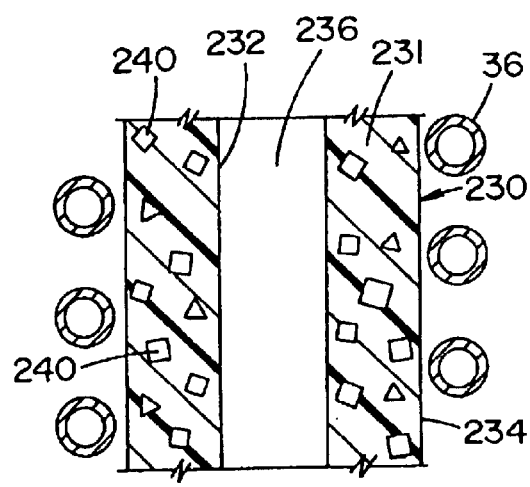
FIG. 12 is an enlarged sectional view of a portion of a vaporizer heating tube comprised of metal flakes embedded within an electrically non-conductive material.
Figure 13:
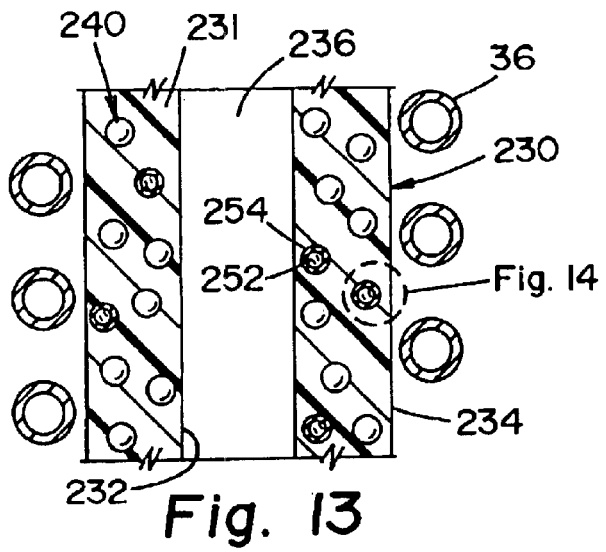
FIG. 13 is an enlarged sectional view of a portion of a vaporizer heating tube comprised of metal coated glass spheres embedded within an electrically non-conductive material.
Figure 14:
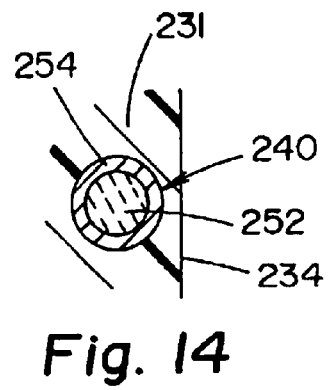
FIG. 14 is an enlarged view of the area shown in FIG. 14.

Other methods for increasing the heated surface area and/or creating turbulence which brings the liquid into contact with the heated surface and encourages mixing with the carrier gas are also contemplated. In the embodiment of FIG. 8, a deflecting member or insert 180 in the shape of a helix or auger is axially mounted within the bore 34. The insert 180 is preferably inductively heated as well as or in place of the tube 30 (or block 140, where present). For example, the helix 180 is formed from stainless steel or other electrically conductive material which is not susceptible to degradation by the liquid or vapor passing through the bore. In the embodiment of FIG. 8, turns 181 of the corkscrew increase in diameter in the direction of flow. For example, the last turn is close to or touching the tube 30.

Figure 9:
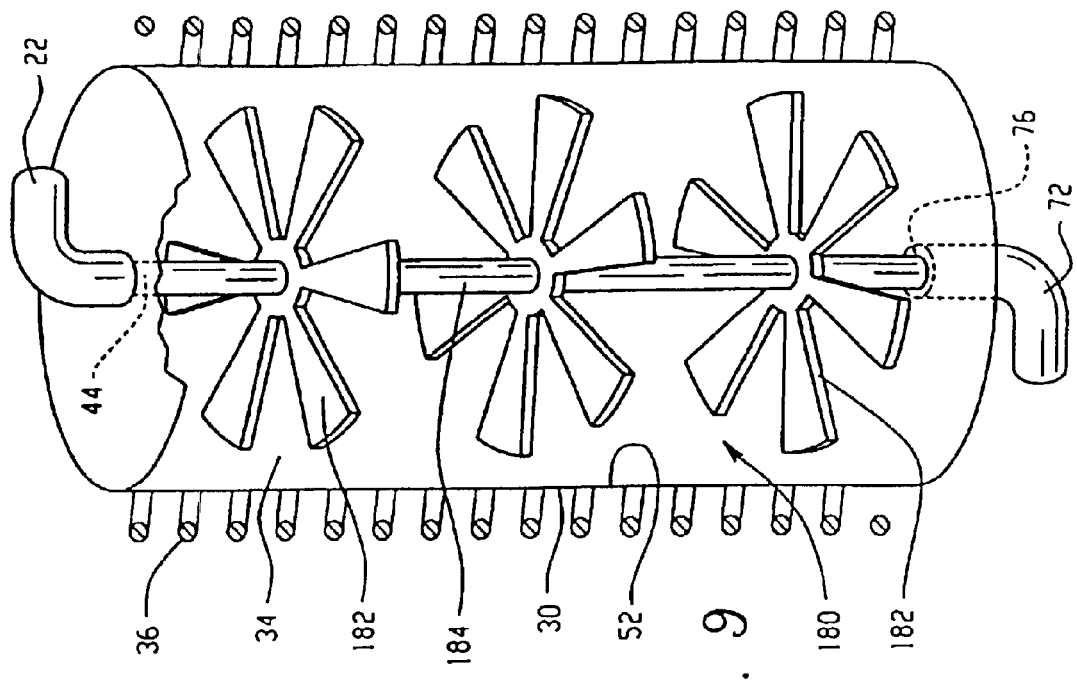
FIG. 9 is a perspective view of an eighth embodiment of a vaporizer.

In an alternative embodiment, shown in FIG. 9, an insert 180 is axially mounted in the bore 34 and includes axially spaced disks or plates 182 mounted to a central shaft 184. In yet another embodiment, baffles or fins may be provided to reduce the available flow space while increasing the heated surface area. For example, as shown in FIG. 2, baffles 186 extend from the walls of the tube into the bore. The baffles may transfer heat by conduction and/or may be inductively heated in the same manner as the tube 32.

To increase heat flow to the insert 180 in the embodiments of FIGS. 8 and 9, the insert is preferably attached to the tube 30 by thermally conductive members 188, such as metal screws (FIG. 8). For example, threads are tapped in the tube 30 and adjacent ends of the insert 180. Thermally conductive screws are then inserted through corresponding tapped threads and thus create a path for the travel of heat to the insert. Countersinking the heads of the screws and/or soldering or brazing over the screw heads creates a smooth surface which allows the induction coil 36 to be closely spaced from the tube 30.

The water, liquid hydrogen peroxide, or other vaporizable liquid, vaporizes as it contacts the wall surface 52 of the bore 34 and is progressively converted from a liquid, spray, or mist to a vapor. The increasing pressure which would normally result from this conversion is substantially eliminated by the increase in size of the bore and/or by an increase in flow velocity such that the flow through the bore is maintained. At the end of the series of passes through the bore 34, the water and/or hydrogen peroxide is preferably entirely in vapor form at a temperature and pressure which maintain the vapor below the dew point, such that condensation of the vapor does not occur.

The vaporizer 12 is capable of achieving a higher vapor output than conventional, drip-type vaporizers which are heated by a resistance-type heater. The heating rate which can be achieved using an induction coil 36 is significantly higher than that which can be achieved with resistance heaters. Obviously, as the heat supplied increases, correspondingly higher outputs can be achieved.

It will be appreciated that the vapor generator of any of the above embodiments is alternatively coupled with a large enclosure, such as a room, or temporary enclosure surrounding a large item to be microbially decontaminated. This is particularly true when a sterilant vapor, such as hydrogen peroxide, is used which is effective at or about room temperature (i.e., from about 15–30° C.) and at or close to atmospheric pressure.

Sterilizable enclosures include microorganism-free or near microorganism-free work areas, freeze dryers, and pharmaceutical or food processing equipment. Whether high sterilization temperatures and/or evacuation of the enclosure during sterilization are feasible depends on the construction of the enclosure and the nature of its contents. For example, sterilizable work areas are, in some instances, constructed of non-rigid plastic materials which do not withstand high temperatures and large pressure gradients. Food processing equipment, in contrast, is often required to withstand high temperatures and pressures during processing operations and is more easily adapted to achieving optimal sterilization conditions through evacuation and heating. sing one or more of such vaporizers 12, a high speed bottling line (e.g., about 1000 bottles/min) can be decontaminated.

For example, the chamber 14 may be a room having a volume on the order of 1,000–4,000 cubic meters. In this embodiment, the combined carrier gas streams may have a flow rate of about 20,000 liters/minute, while the carrier gas stream flowing through the vaporizer 12 is 100 liters/min or less, more preferably, about 20 liters/min or less, most preferably, about 1–10 liters/min.

Optionally, the pathways 22, 24, 102 include all or a portion of the duct work of a pre-existing HVAC system. Upon initiating a decontamination process, air from the room is circulated through the dryer 122 for a sufficient duration to bring the relative humidity in the room down to an acceptable level, preferably below 20% relative humidity. For sealed enclosures, pressure control within the enclosure may be appropriate. For decontamination of clean rooms and the like, where drawing potentially contaminated air into the room is to be avoided, the pressure in the room is preferably maintained above ambient pressure. Where hazardous materials have been used or exposed in the room to be treated, a below atmospheric pressure is preferably maintained in the room 14 to ensure that the hazardous materials do not escape prior to decontamination.

Once the room 14 has been brought to a sufficiently low relative humidity, an antimicrobial vapor is injected into the air. The antimicrobial vapor includes hydrogen peroxide vapor in one embodiment, although other antimicrobial vapors or mixtures of antimicrobial vapors are also contemplated.

The controller 60 is connected with one or more peroxide concentration sensors 128 in the room. The controller optionally controls fans (not shown) or other devices in the room 10 for adjusting the distribution of hydrogen peroxide vapor for better uniformity.

When the air recirculation ducts are larger in diameter and have a higher air moving capacity, a second flash vaporizer 12 and a second injection pump 80 are connected with the liquid peroxide source 70 and with the air source. For larger enclosures, one or more additional air circulation lines with flash vaporizers are provided.

While described with particular reference to hydrogen peroxide, it will be appreciated that the system of the present invention is also applicable to vaporization of other solutions and pure liquids, such as peracetic acid, other peroxy compounds, and the like.

A plurality of further contemplated embodiments of the present invention will now be described with particular reference to FIGS. 10–24. In accordance with the further contemplated embodiments of the present invention, a vaporizer heating apparatus comprised of a heating tube and/or an insert that includes an electrically non-conductive material and an electromagnetically responsive material, as will be described in detail below. It should be understood that in each of the further contemplated embodiments, the insert is optionally provided. The term "electromagnetically responsive material" is used herein to refer to a material that responds to the presence of an electric field, a magnetic field or both, such that thermal energy is produced upon exposure to at least one of the aforementioned fields. The electric and magnetic fields may be static or oscillatory.

The further contemplated embodiments of the present invention may take a variety of forms, including, but not limited to, those discussed in detail below. According to one further contemplated embodiment, tube 30 and/or insert 180 is/are comprised of an electrically non-conductive material and an electromagnetically responsive material, wherein the electromagnetically responsive material is embedded in the electrically non-conductive material. In another further contemplated embodiment, a layer of electromagnetically responsive material may provide an external surface of tube 30 and/or insert 180, or may be located inside of an electrically non-conductive material. In still another further contemplated embodiment, a layer of electrically non-conductive material isolates the electromagnetically responsive material from antimicrobial fluids. In this regard, an electrically non-conductive material is used to provide a protective coating layer.

It should be appreciated that elements of the foregoing contemplated embodiments may be used in alternative combinations. Illustrative embodiments are described in detail below.

The electrically non-conductive material may take many suitable forms, including, but not limited to, a polymeric material, a ceramic material or a glass. Furthermore, a polymer, a ceramic and/or a glass may be used in combination to form tube 30 and/or insert 180.

Suitable polymers include, but are not limited to, a thermoplastic polymer or a thermoset polymer.

By way of example, and not limitation, a thermoplastic polymer forming the electrically non-conductive material may be selected from the group consisting of: a nylon; Amodel® (PPI, polyphthalamide); Aurum® (polyimide); Ryton®/Fortron® (PPS, polyphenylenesulphide); Fluoropolymers (PFA, FEP, Tefzel® ETFE, Halar® ECTFE, Kynar® PVDF); Teflon® PTFE; Stanyl® (4.6 polyamide, 4.6 Nylon); Torlon® (polyamide-imide); Ultem® (polyetherimide, PEI); Victrex® PEEK (polyaryletherketone, polyetheretherketone); or any other thermoplastic polymers having a "use temperature" above the highest temperature needed to produce an antimicrobial vapor. As indicated above, the antimicrobial vapor may be produced from water alone, or a mixture of fluids such as water and hydrogen peroxide. In most cases, it is expected that thermoplastic polymers having a use temperature above about 150° C. should be suitable. For example, nylons have a short term use temperature of about 199° C. For certain sterilants, heat stabilized nylon 6/6, which has a continuous use temperature of 121° C., may be sufficient. Teflon has a continuous use temperature of 260° C.

The thermoset polymer forming the electrically non-conductive material may be selected from the group including, by not limited to, an epoxy or a urethane.

By way of example, and not limitation, a suitable ceramic material for forming the electrically non-conductive material may be selected from the group consisting of: silica, alumina, magnesia or other metal-oxide based materials.

The electromagnetically responsive material may take many suitable forms, including, but not limited to, a metal or metal alloy, a metal coated material, carbon, graphite, stainless steel, a metal alloy solder (e.g., tin and zinc), a ferromagnetic material (e.g., iron), a ferrimagnetic material (i.e., ferrites, such as magnetite ($Fe_3O_4$) or $FeO.Fe_2O_3$), a ferroelectric material (such as perovskites, e.g., lead titanate ($PbTiO_3$)), a ferrielectric material, and combinations thereof.

By way of example, and not limitation, the metal may be selected from the group consisting of: nickel, copper, zinc, silver, stainless steel, tungsten, nichrome (nickel-chromium alloy), and combinations thereof.

As indicated above, a metal alloy solder can be used as an electromagnetically responsive material. The solder melts during processing of the electrically non-conductive material (e.g., a polymer, a ceramic or glass) to form an interconnecting metallic network within the electrically non-conductive material. In the case of a polymer, a low melting solder is combined with the polymer resin and processed. For example, a polymer and a low melting solder can be extruded into strands. The strands are cooled and chopped into pellets. The pellets are then injection molded into a heating tube and/or insert. The low melting solder forms an interpenetrating metallic network within the polymer.

In the case of a ceramic, the porosity of the ceramic allows the solder to flow within the ceramic when the ceramic is calcined, thus producing a calcined ceramic having a metallic network. The pre-calcining porosity of the ceramic helps the solder to flow within the ceramic during calcining. It should be appreciated that the solder should have a melt temperature that is above the highest temperature needed to vaporize the antimicrobial fluids.

Metals other than solder can also be used to produce the metallic network. In this regard, any metal that will melt when the ceramic is calcined is also suitable. Since the calcining temperature of most ceramics is typically in the range of 2,500° F. to 3,000° F., most metals will melt during calcining. Upon cooling, the metal re-crystallizes forming an interpenetrating, metallic network within the ceramic.

Carbon is also a suitable electromagnetically responsive material for use with a polymer, a ceramic or glass matrix. In this regard, carbon can be added to the polymer, ceramic, or glass to produce a network of conductive carbon particles. Since carbon is also a refractory, the carbon particles will withstand the high calcining temperatures of the ceramic. Carbon is also thermally conductive, and thus will help to diffuse heat (produced by induction heating). The carbon also provides a good receiving "antenna" for electromagnetic waves.

As discussed above, one further contemplated embodiment of the present invention includes a tube 30 and/or insert 180 that are comprised of an electrically non-conductive material and an electromagnetically responsive material, wherein the electromagnetically responsive material is embedded in the electrically non-conductive material (e.g., a polymer, a ceramic or a glass matrix) to form a composite material. The electromagnetically responsive material may take the form of a particulate, including, but not limited to fibers, flakes, spheres, whiskers, grains or combinations thereof, wherein the particulate is a metal or metal alloy, a metal coated particle, carbon, or graphite. The particulate may take a variety of shapes, including, but not limited to, spherical, oblate and prolate. Furthermore, the electromagnetically responsive material may alternatively coat a particulate (i.e., metal or metal alloy, carbon or graphite coated particulates).

Examples of specific suitable particulates, include, but are not limited to, carbon particulates (fibers, flakes, whiskers or grains); nickel particulates (fibers, flakes, whiskers, or grains); tungsten particulates (fibers, flakes, whiskers or grains); nichrome (wires, fibers, flakes, whiskers, or grains); nickel, copper or silver coated (autocatalytically or by electrodeposition) glass spheres; nickel, copper or silver coated (autocatalytically or by electrodeposition) thermoplastic polymer particulate; steel flakes; and stainless steel fibers.

In one embodiment, the electromagnetically responsive particulate is embedded in the electrically non-conductive material in a concentration suitable to provide a heating apparatus having a desired heating characteristic. As will be appreciated, the heat generating and heat transfer characteristics of the heating apparatus are based upon the concentration (i.e., loading) of electromagnetically responsive particulate within the electrically non-conductive material. It is believed that the heat transfer (i.e., thermal conductivity) characteristics of the heating apparatus are related to the electrical conductivity characteristics of the heating apparatus. Accordingly, the concentration of the electromagnetically responsive particulate in the heating apparatus may be determined in accordance with percolation theory.

According to percolation theory, when the concentration of the electromagnetically responsive particulate reaches the percolation threshold, the electrical conductivity of the composite will rise precipitously. Therefore, when rapid heating is desired, the concentration of the electromagnetically responsive particulate is preferably at or above the percolation threshold. Likewise, if a longer heating time is desired or acceptable, then the concentration of the electromagnetically responsive particulate may be below the percolation threshold.

In the case of a particulate loaded composite, the mathematical model that describes the electrical behavior of the composite is known as percolation theory. For example, if particles of metal are deposited on a substrate in an L×L array of holes, electrical conduction can occur between the metal particles, because when two adjacent holes are filled with a metal particle, they just barely touch each other, thereby allowing electrical conduction between the metal particles. Groups of touching metal particles are referred to as "clusters." A cluster which extends from one end of the array to the other is called a "spanning cluster."

When metal particles are initially deposited into the holes of the L×L array there can be no electrical conduction. In this regard, electrical conduction cannot occur until at least L metal particles have been deposited. However, in view of the statistical probability of L metal particles aligning themselves to form a spanning cluster, many more than L metal particles will need to be deposited before the probability of a spanning cluster becomes significant. At some point there is an exponential increase in the electrical conduction. The "percolation threshold" is the concentration of electromagnetically responsive particulate that results in an electrically conductive composite.

The percolation threshold depends on the aspect ratio (i.e., the ratio of the longest dimension to the shortest dimension) of the particulate. In this respect, it is believed that the percolation threshold for electrically conductive spheres (aspect ratio of one) is greater than the percolation threshold for fibers. Accordingly, a higher concentration of electrically conductive spheres is needed to achieve an electrically conductive composite than would be required for electrically conductive fibers.

The scaling relationship (i.e., power law) for electrical conductivity of a particulate loaded matrix is expressed as $\sigma \propto (x-x_c)^t$, where $\sigma$ is the electrical conductivity, x is the concentration (volume percent) of electromagnetically responsive particulate, $x_c$ is the percolation threshold ($x_c$ is dependent on the geometry of the particle), and t is a corresponding critical exponent. Typically, t is about 2.0.

Under conventional percolation theory, when the concentration of the electromagnetically responsive particulate reaches the percolation threshold, the electrical conductivity of the composite rises precipitously. This scaling law applies to the application of both direct current (DC) and alternating current (AC).

It should be appreciated that most composites have a non-zero electrical conductivity at concentrations of electromagnetically responsive particulate below the percolation threshold. It is believed that this results from a percolation cluster that consists of the nearest-neighbors sub-network of the full tunneling network. While the concentration of electromagnetically responsive particulate is preferably selected to be equal or greater than the percolation threshold, the concentration may also be selected to be less than the percolation threshold, as long as a non-zero electrical conductivity is obtained.

It is believed that the conduction mechanism of the composite is not by actual particle to particle contact. In this regard, there is a thin layer of electrically non-conductive material between some of the electromagnetically responsive particles. Accordingly, the electrons (which are the charge carriers in the composite) must quantum mechanically tunnel from one particle to another through an intervening layer of electromagnetically responsive material. Accordingly, the electrical conductivity of the composite may not be as good as the electrical conductivity of the electromagnetically responsive material alone, i.e., the material from which the particles are made.

It should be understood that the dimensionality of the electromagnetically responsive network may have a "fractal" (i.e., has a dimensionality of between two and three) value. In other words, a network of electromagnetically responsive particles within an electrically non-conductive material may have a dimensionality of somewhere between two and three, where a dimensionality of two is the dimensionality of a square, and a dimensionality of three is the dimensionality of a cube.

It is further believed that a polymer with electromagnetically responsive particles embedded therein may also act as a current limiting polymer to self-limit heat build-up, and thereby prevent melting of the polymer. In this respect, a sufficient quantity of electromagnetically responsive particulates are blended within a polymer matrix such that when desired operational parameters are obtained, the vaporizer operates as a current limiting polymer. In other words, as the temperature of the vaporizer increases beyond the operating temperature, the polymer matrix heats and expands to the point where the electromagnetically responsive particles lose sufficient "contact" such that the electrical conductivity of the composite material decreases, thus limiting the current flowing through the composite material, and thereby limiting the joule heat produced. In this instance, the polymer matrix begins to cool until the polymer matrix contracts sufficiently for particle to particle contact to be restored, in which case the vaporizer becomes operational again.

As indicated above, an AC source 50 supplies an alternating current to a coil 36. Electromagnetic radiation causes electrons to move in the electromagnetically responsive material, thereby resulting in the production of heat. Electromagnetically responsive materials couple to either an electric field or an oscillating magnetic field to produce the heat. In the case of coupling to an electric field, the heat produced is joule heat or $I^2R$ heat. In the case of coupling to an oscillating magnetic field, heat is produced through the generation of eddy currents in the electromagnetically responsive material. It should be appreciated that, depending on the electromagnetically responsive particles used, a microwave or RF generator that directs radiation toward the electromagnetically responsive material may be substituted for coil 36.

It should be appreciated that the frequency of the alternating current can be varied, thereby causing the applied electromagnetic radiation to penetrate heating tube 30 and/or insert 180 at various depths, as a result of "skin effect." Skin effect will now be described by way of the following example, where the vaporizer is comprised of a heating tube 30 and an insert 180. Heating tube 30 and/or insert 180 may include electromagnetically responsive material.

EXAMPLE 1 heating tube: geometry: cylindrical
wall thickness=5 mm
material: resin bonded graphite $$\text{(skin depth)(square root of frequency)}=\delta\sqrt{\sqrt{f}}=1.592$$

where δ is the skin depth, and f is the frequency of the electromagnetic radiation applied to the heating tube of Example 1. At a frequency of f=101.4 kHz, the applied electromagnetic radiation will have decreased to 1/e its initial value within the wall thickness of tube 30 (i.e., 5 mm). To energize electromagnetically responsive material in the insert, electromagnetic radiation of a frequency ($f_1$) less than 101.4 kHz should be used. In this regard, a frequency ($f_1$) less than 101.4 kHz will result in a skin depth greater than the 5 mm wall thickness of tube 30. Accordingly, the emitted radiation has a wavelength that allows propagation through tube 30, and will impinge directly on electromagnetically responsive material in insert 180. Thus, insert 180 is heated directly by induction, rather than by conduction. It should be understood that the frequency of the electromagnetic radiation may be varied such that only tube 30 is exposed to electromagnetic radiation at a first frequency, and tube 30 and insert 180 are exposed to electromagnetic radiation at a second frequency. Accordingly, the frequency of the electromagnetic radiation can be varied to alternately heat (1) tube 30 and (2) tube 30 and insert 180.

Referring now to FIG. 10, there is shown a vaporizer 12 having a tube 230 comprised of an electrically non-conductive material 231 embedded with electromagnetically responsive particles 240. In the illustrated embodiment, electrically non-conductive material 231 is a polymer, and electromagnetically responsive particles 240 are metal fibers. Tube 230 includes an inner surface 232 and an outer surface 234. Inner surface 232 defines a bore 236.

FIGS. 11–14 illustrate tube 230, wherein alternative particle types are used for electromagnetically responsive particles 240. In this regard, FIG. 11 shows electromagnetically responsive particles 240 in the form of granular metal particles, embedded in electrically non-conductive material 231.

FIG. 12 shows a heating tube 230 comprised of electromagnetically responsive particles 240 in the form of metal flakes, embedded in electrically non-conductive material 231.

FIG. 13 shows a heating tube 230 comprised of electromagnetically responsive particles 240 in the form of metal coated spheres, embedded in electrically non-conductive material 231. The metal coated spheres are generally comprised of a glass spheres 252 coated with a metal coating 254, as best seen in FIG. 14. As discussed above, glass spheres 252 may be coated with an electromagnetically responsive material autocatalytically or by electrodeposition.

Referring now to FIG. 15, there is shown a heating tube 230 comprised of an electrically non-conductive material 231 embedded with electromagnetically responsive particles 240, and a layer 260 of electromagnetically responsive material. Layer 260 of electromagnetically responsive material is formed on inner surface 232 of tube 230. Layer 260 may be formed by conventionally known deposition techniques (discussed below), or may be a preformed component. In the illustrated embodiment, electromagnetically responsive particles 240 are metal fibers.

Referring now to FIG. 16 there is shown a heating tube 230 comprised of an electrically non-conductive material 231 embedded with electromagnetically responsive particles 240, and a layer 270 of electrically non-conductive material on inner surface 232 of tube 230. In this embodiment of the present invention, layer 270 of electrically non-conductive material (e.g., a polymer) isolates antimicrobial fluids from electromagnetically responsive particles 240. In this regard, only layer 270 of electrically non-conductive material is exposed to the antimicrobial fluids. By way of example, and not limitation, layer 270 of electrically non-conductive material may be applied to inner surface 232 by conventionally known deposition techniques. Alternatively, layer 270 of electrically non-conductive material may be preformed (e.g., by molding).

FIG. 17 illustrates a tube 309 including a tube wall 32 comprised of an electromagnetically responsive material, such as iron, zinc, carbon steel, stainless steel, aluminum, copper, brass, or bronze, as discussed above in connection with tube 30. A layer 270 of electrically non-conductive material lines inner surface 52 of tube wall 32. In this manner, layer 270 of electrically non-conductive material isolates the electromagnetically responsive material from antimicrobial fluids. Accordingly, only layer 270 of electrically non-conductive material is exposed to antimicrobial fluids. By way of example, and not limitation, layer 270 of electrically non-conductive material may be coated onto inner surface 232 by conventionally known deposition techniques. Alternatively layer 270 of electrically non-conductive material may be preformed (e.g., by molding).

FIG. 18 illustrates an embodiment of the present invention, wherein microwave energy is generated to produce heat. Tube 230 is preferably comprised of electrically non-conductive material 231 having electromagnetically responsive particles 240 embedded therein. The electromagnetically responsive material 231 is preferably a material that produces heat as the material is driven through its electric or magnetic hysteresis loop.

A microwave generator 250 provides a source of electromagnetic energy. Microwave generator 250 may take the form of a magnetron that generates electromagnetic energy. Microwave generator 250 generates microwaves, i.e., electromagnetic radiation having a frequency of about 1 GHz to about 300 GHz. In one embodiment, glass containing ferrite particles is exposed to microwaves. It is believed that the changing magnetic field of the microwaves drives the ferrite particles through their magnetic hysteresis loops, thus magnetically working the particulates. This magnetic working results in the ferrite particles heating up. The heat is transferred to the glass (e.g., Pyrex®) matrix. In a similar manner, ferroelectric particulate can be mixed within a polymer, a ceramic or glass matrix. In this case, it is believed that the oscillating electric field of an incident electromagnetic wave drives the particles through their electric hysteresis loops generating heat.

Electromagnetically responsive material 231 may be selected from the group, including, but not limited to: a ferromagnetic (iron) and/or a ferrimagnetic material (ferrites, e.g., magnetite ($Fe_3O_4$) or $FeO \cdot Fe_2O_3$), or a ferroelectric (such as perovskites, e.g., lead titanate ($PbTiO_3$)) and/or a ferrielectric material. One specific exemplary material is metalized polyethylene terephthalate (PET), commonly used in microwavable food packages to speed the cooking process.

Figure 18:
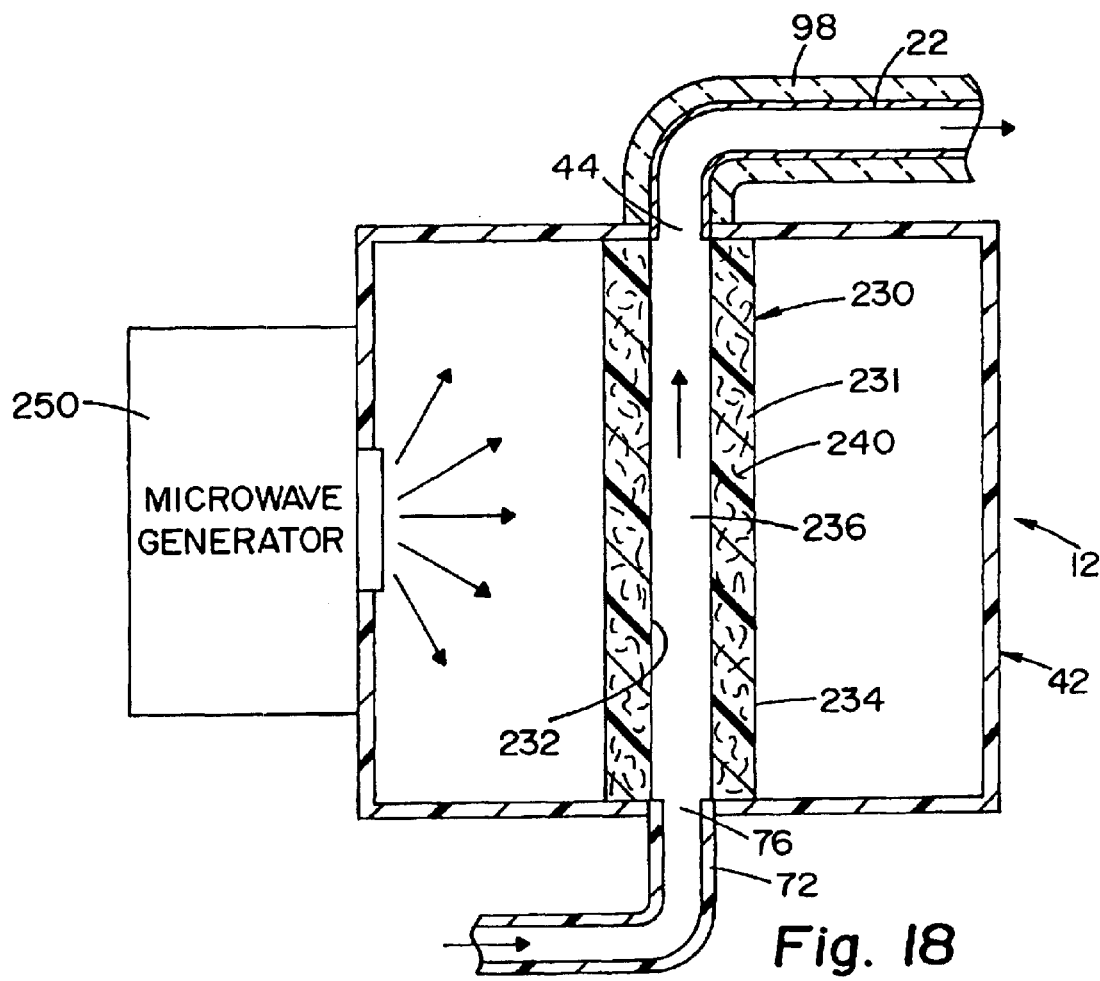
FIG. 18 is a sectional view of a vaporizer including a microwave generator, according to yet another embodiment of the present invention.

As an alternative to the embodiment illustrated in FIG. 18, tube 230 may be comprised of an electrically non-conductive material 231, but without any embedded electromagnetically responsive particles. A layer of electromagnetically responsive material 240 (e.g., a metalized polymeric film, such as metalized PET) coats inner surface 232 of tube 230.

Figure 15:
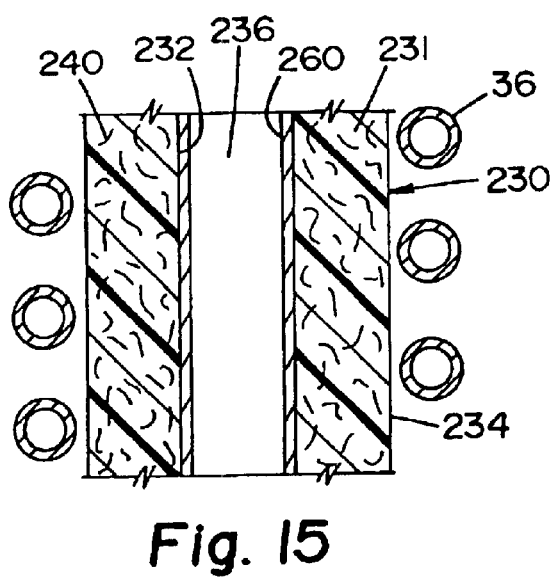
FIG. 15 is an enlarged sectional view of a vaporizer for use in a microbial decontamination process, according to still another embodiment of the present invention.
Figure 16:
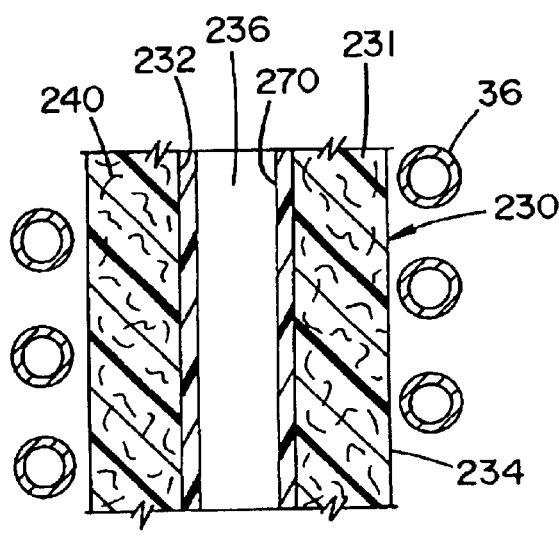
FIG. 16 is an enlarged sectional view of a vaporizer for use in a microbial decontamination process, according to still another embodiment of the present invention.
Figure 17:
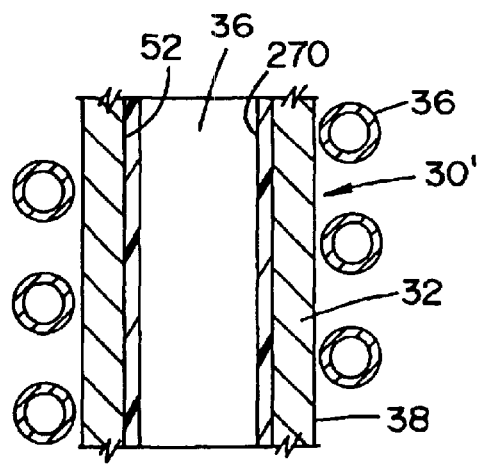
FIG. 17 is an enlarged sectional view of a vaporizer for use in a microbial decontamination process, according to still another embodiment of the present invention.

As indicated above, the electromagnetically responsive material may be in the form of a layer of material on a surface of heating tube 30 and/or insert 180 (e.g., see FIG. 15). The electrically non-conductive material may alternatively be in the form of a protective coating layer on a surface of heating tube 30 and/or insert 180 (e.g., see FIGS. 16 and 17). Layers of electromagnetically responsive material and electrically non-conductive material may be formed by conventionally known deposition techniques, including, but not limited to electrodeposition, autocatalytic deposition, arc spraying, and thermal spraying.

According to the further contemplated embodiments of the present invention, the heating tube and/or insert may be produced by a variety of techniques, including, but not limited to conventional molding, injection molding, or extrusion. Extrusion or injection molding are preferred for a thermoplastic polymer. Conventional molding is preferred in the case of a thermosetting polymer. In the case of an extruded tube or insert, electromagnetically responsive particulate can be added to an extruder along with a polymer to produce a cylinder of a composite material.

Figure 19:
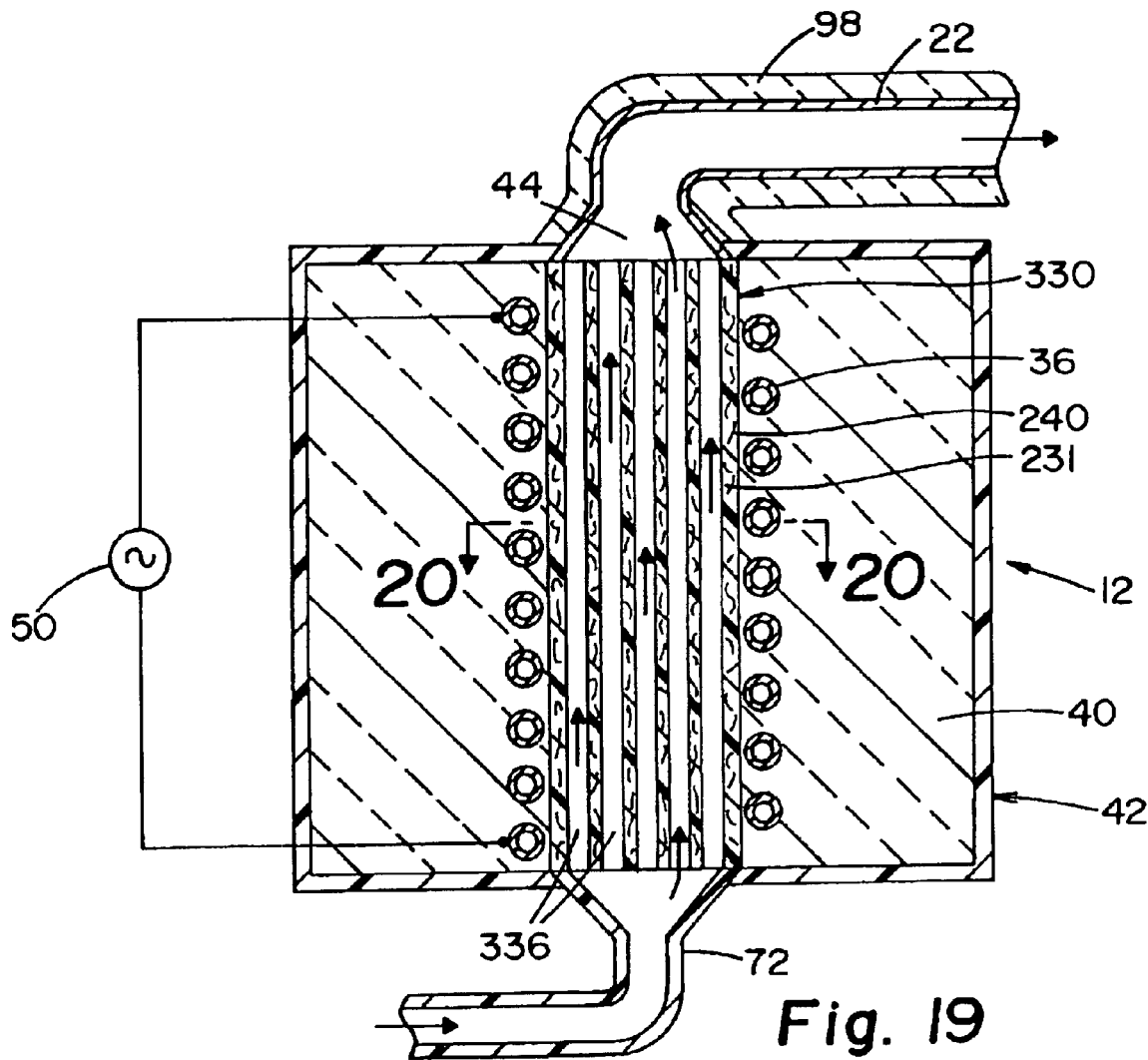
FIG. 19 is a sectional view of a vaporizer for use in a microbial decontamination process, according to yet another embodiment of the present invention.
Figure 20:
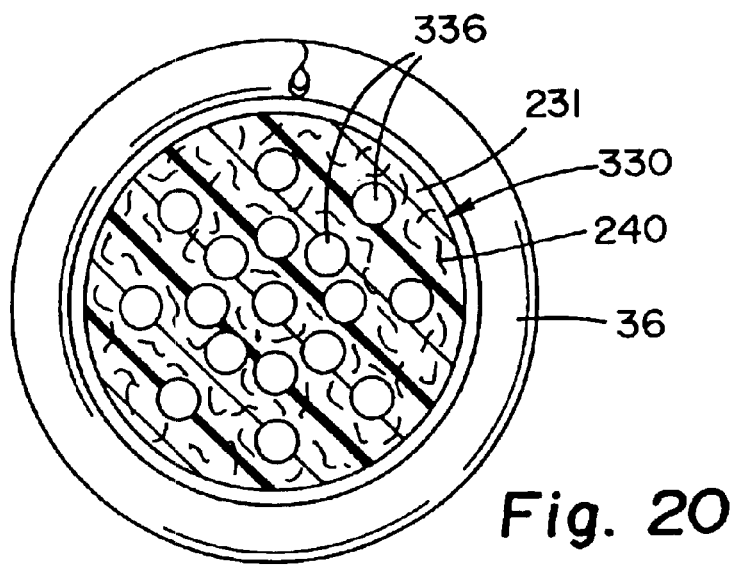
FIG. 20 is a sectional view taken along lines 20—20 of FIG. 19.

FIGS. 19 and 20 illustrate a heating tube 330 having multiple bores 336 formed therein to provide multiple pathways. Tube 330 is comprised of electromagnetically responsive particles 240 embedded in an electrically non-conductive material 231. Heating tube 330 may be produced by conventionally known means, including, but not limited to molding, injection molding, extrusion and spin casting. Bores 336 may be formed therein by drilling.

Figure 21:
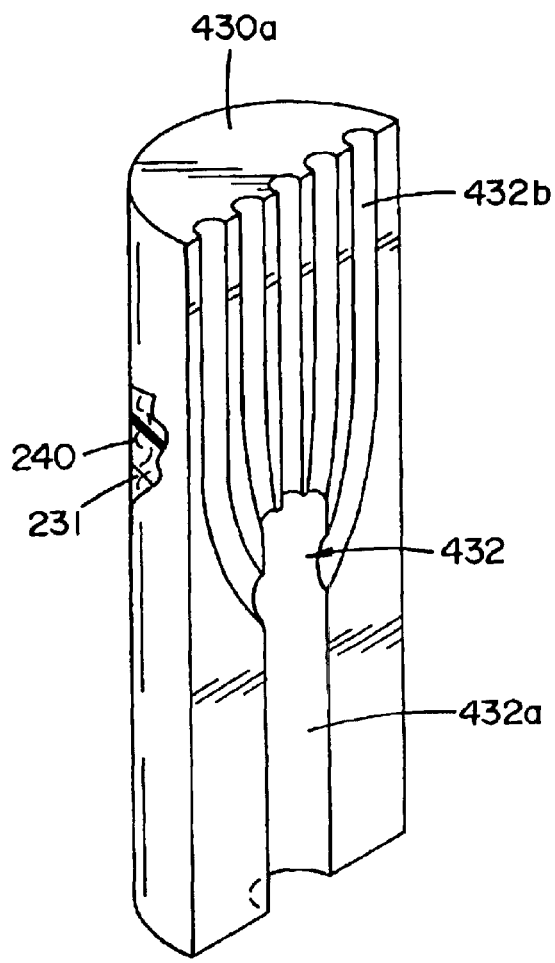
FIG. 21 is a perspective view of a vaporizer heating tube section comprised of electromagnetically responsive material embedded in an electrically non-conductive material, according to a still further embodiment of the present invention.
Figure 22:
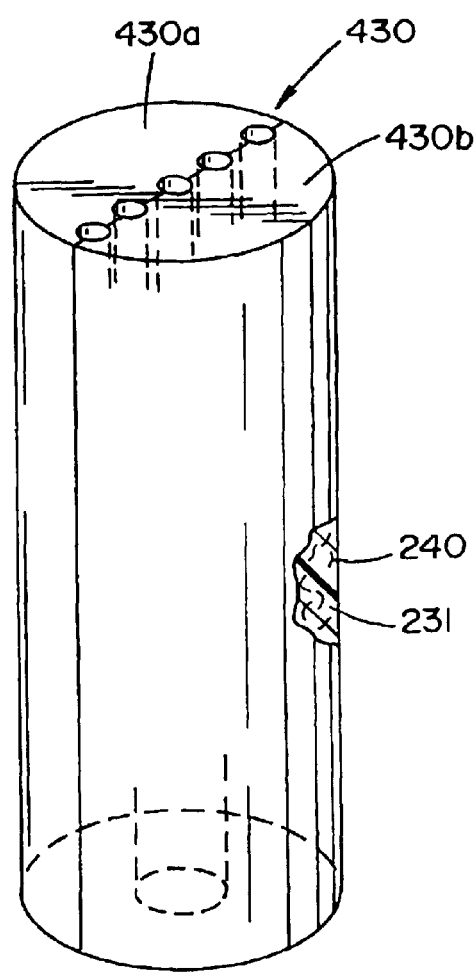
FIG. 22 is a perspective view of a vaporizer heating apparatus formed from two heating tube sections of the type shown in FIG. 21.

FIGS. 21 and 22 illustrate yet another embodiment of the heating tube. Tube 430 is comprised of electromagnetically responsive particles 240 embedded in an electrically non-conductive material 231. Tube 430 is formed of two half-cylinder portions 430*a*, 430*b* with grooves 432 machined therein. Grooves 432 include a single groove portion 432*a* and a multi-groove portion 432*b*. Heating tube 430 may be produced by molding, injection molding, or extrusion. The two half-cylinder portions 430*a*, 430*b* may be joined ultrasonically or otherwise (FIG. 22) to form a cylinder with veins that act as flow paths. Atomized antimicrobial fluids can be dispersed into the veins. It should be appreciated that additional flow paths may be formed by machining.

Figure 23:
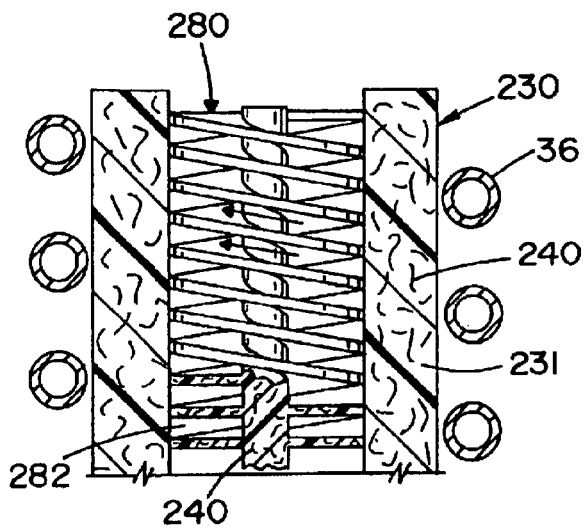
FIG. 23 is a sectional view of a portion of a vaporizer heating apparatus assembly, according to a still further embodiment of the present invention.
Figure 24:
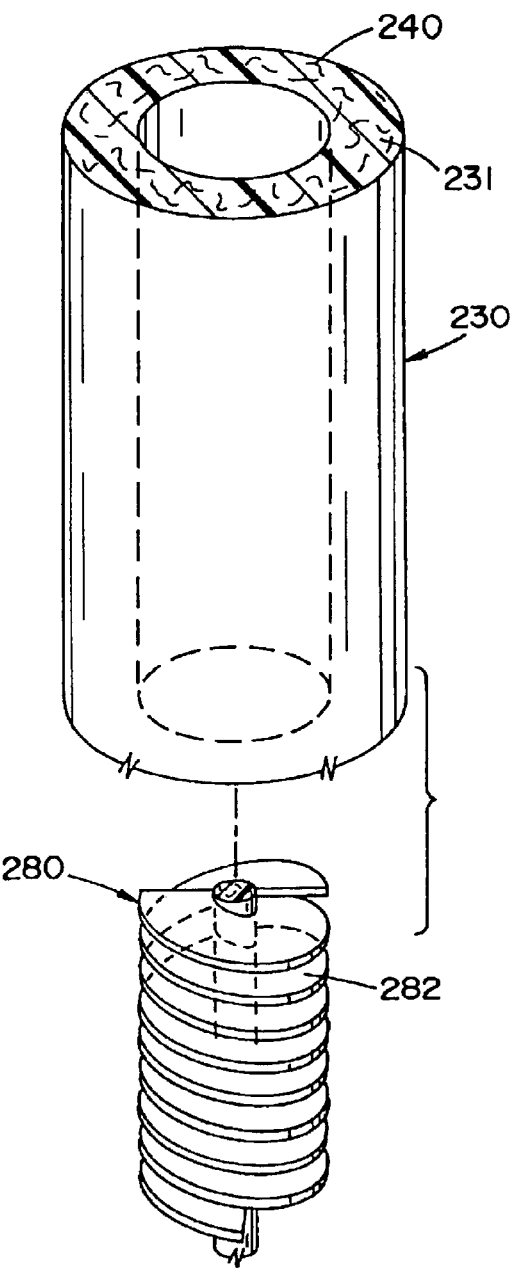
FIG. 24 is an exploded perspective view of the vaporizer heating apparatus assembly shown in FIG. 23.

FIGS. 23 and 24 illustrate tube 230 comprised of electromagnetically responsive particles 240 embedded in an electrically non-conductive material 231. A screw-shaped insert 280 is comprised of electromagnetically responsive particles 240 embedded in an electrically non-conductive material 231. A spiral passageway 282 is defined by screw-shaped insert 280. Atomized antimicrobial fluids can be dispersed into spiral passageway 282. As shown in FIG. 24, insert 280 is located inside tube 230.

The heating tube and/or insert may have geometric shapes other than those illustrated herein. Furthermore, use of an electrically non-conductive material that can be molded or extruded (e.g., a polymer) facilitates production of heating tubes and inserts of a wide variety of geometric shapes. This also allows the heating tube and insert to be conveniently formed as an integrated component. It should also be appreciated that one or more elbows may be attached to a cylindrical heating tube and/or insert, wherein the elbow provides a "wall" upon which an atomized antimicrobial fluid can impinge and thus vaporize.

It should be understood that the present invention may also include a temperature sensing device to prevent overheating of the vaporizer that could result in melting or destruction of any electrically non-conductive material. One exemplary temperature sensing device is a thermocouple that senses temperature changes by using a pair of joined wires made of dissimilar metals that produces a voltage that changes with temperature.

Use of an electrically non-conductive material as described above may provide several advantageous effects. In this regard, the vaporizer weight and manufacturing costs can be reduced. Furthermore, electrically non-conductive material can be used to insulate electromagnetically responsive material from antimicrobial fluids. Accordingly, antimicrobial fluids such as water, hydrogen peroxide, peracids, and the like can be used without concern about degradation to the antimicrobial fluids by the electromagnetically responsive material (e.g., copper).

The invention has been described with reference to preferred embodiments. Obviously, modifications and alterations will occur to others upon reading and understanding the preceding detailed description. It is intended that the invention be construed as including all such modifications and alterations insofar as they come within the scope of the appended claims or the equivalents thereof. Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. A vaporizer for vaporizing an atomized, antimicrobial liquid, to form an antimicrobial vapor, the vaporizer comprising:

a source of electromagnetic radiation;

a heating chamber having a passage formed therethrough, said heating chamber having an inlet for receiving the atomized antimicrobial liquid into the passage, and an outlet for releasing the antimicrobial vapor from the passage to supply the antimicrobial vapor to a defined region, wherein said heating chamber is comprised of a first electrically non-conductive material and a first electromagnetically responsive material; and an insert located within the passage of the heating chamber, said insert comprised of at least one of:

(1) a metals, and (2) a second electrically non-conductive material and a second electromagnetically responsive material, wherein said heating chamber and said insert both contribute to vaporization of the atomized, antimicrobial liquid to form the antimicrobial vapor.

2. A vaporizer as defined by claim 1, wherein at least one of said first and second electrically non-conductive material is selected from the group consisting of: a polymer, a ceramic and a glass.

3. A vaporizer as defined by claim 2, wherein said polymer is selected from the group consisting of: a thermoplastic polymer and a thermosetting polymer.

4. A vaporizer as defined by claim 3, wherein said thermoplastic polymer is selected kern the group consisting of:

polyphthalamide, polyimide, Fluoropolymers, PTFE, 4.6 polyamide, 4.6 Nylon, polyamide-imide, polyaryletherketone, polyetheretherketone.

5. A vaporizer as defined by claim 3, wherein said thermosetting polymer is selected from the group consisting of: an epoxy and a urethane.

6. A vaporizer as defined by claim 2, wherein said ceramic is a metal-oxide material.

7. A vaporizer as defined by claim 6, wherein said ceramic is selected from the group consisting of: silica, alumina, and magnesia.

8. A vaporizer as defined in claim 1, wherein said first and second electromagnetically responsive material is selected from the group consisting of: a metal, a metal alloy, a metal coated material, carbon, graphite, stainless steel, a metal alloy solder, a ferromagnetic material, a ferrimagnetic material, a ferroelectric material, a ferrielectric material, and combinations thereof.

9. A vaporizer as defined in claim 8, wherein said metal is selected from the group consisting of: nickel, copper, zinc, silver, stainless steel, tungsten, nichrome, and combinations thereof.

10. A vaporizer as defined in claim 1, wherein at least one of said first and second electromagnetically responsive material is a ferromagnetic material.

11. A vaporizer as defined in claim 1, wherein at least one of said first and second electromagnetically responsive material is a ferrimagnetic material.

12. A vaporizer as defined in claim 1, wherein at least one of said first and second electromagnetically responsive material is a ferroelectric material.

13. A vaporizer as defined in claim 1, wherein at least one of said first and second electrically non-conductive material forms an electrically non-conductive matrix, at least one of said first and second electromagnetically responsive material is embedded within the electrically non-conductive matrix.

14. A vaporizer as defined by claim 13, wherein at least one of said first and second electromagnetically responsive material is in the form of a particulate selected from the group consisting of: fibers, flakes, spheres, whiskers, grains, a coated particulate and combinations thereof.

15. A vaporizer as defined in claim 1, wherein at least one of:

said first electromagnetically responsive material forms a layer on a surface of said first electrically non-conductive material, and said second electromagnetically responsive material forms a layer on a surface of said second electrically non-conductive material.

16. A vaporizer as defined in claim 15, wherein at least one of:

said first electromagnetically responsive material is embedded in said first electrically non-conductive material, and said second electromagnetically responsive material is embedded in said second electrically non-conductive material.

17. A vaporizer as defined in claim 15, wherein at least one of: said first electromagnetically responsive material is deposited on said first electrically non-conductive material by at least one of: thermal spraying, electrodeposition, autocatalytic deposition, and arc spraying, and said second electromagnetically responsive material is deposited on said second electrically non-conductive material by at least one of: thermal spraying, electrodeposition, autocatalytic deposition, and arc spraying.

18. A vaporizer as defined in claim 1, wherein at least one of:

said first electrically non-conductive material forms a first layer to provide a first protective coating, said protective coating isolating said first electromagnetically responsive material from an antimicrobial fluid, and said second electrically non-conductive material forms a second layer to provide a protective coating, said second protective coating isolating said second electromagnetically responsive material from an antimicrobial fluid.

19. A vaporizer as defined in claim 18, wherein at least one of:

said first electromagnetically responsive material is embedded in said first electrically non-conductive material, and said second electromagnetically responsive material is embedded in said second electrically non-conductive material.

20. A vaporizer as defined in claim 18, wherein at least one of:

said first electromagnetically responsive material is deposited to form said first layer by at least one of: thermal spraying, electrodeposition, autocatalytic deposition, and arc spraying, and said second electromagnetically responsive material is deposited to form said second layer by at least one of: thermal spraying, electrodeposition, autocatalytic deposition, and arc spraying.

21. A vaporizer as defined in claim 1, wherein said source of electromagnetic radiation is a microwave generator, said microwave generator generating microwaves that cause heating of at least one of said first electromagnetically responsive material and said second electromagnetically responsive material.

22. A vaporizer as defined in claim 21, wherein at least one of:

said first electromagnetically responsive material and said second electromagnetically responsive material is selected from the group consisting of: a ferromagnetic material, a ferrimagnetic material, a ferroelectric material and a ferrielectric material.

23. A vaporizer as defined in claim 1, wherein said source of electromagnetic radiation produces an alternating current.

24. A vaporizer as defined in claim 23, wherein said alternating current has at least a first frequency and a second frequency, wherein said electromagnetic radiation penetrates said heating chamber at respective first and second depths.

25. A vaporizer according to claim 1, wherein said heating chamber includes:

a generally cylindrical tube.

26. A vaporizer according to claim 1, wherein said insert is a screw-shaped insert, said passage following a spiral path through said screw-shaped insert.

* * * * *